(12) United States Patent
Afzal

(10) Patent No.: US 10,809,240 B2
(45) Date of Patent: Oct. 20, 2020

(54) SENSORS FOR MEASURING WATER/SOLUTE CONTENT AND THICKNESS OF PLANT TISSUE

(71) Applicant: The Penn State Research Foundation, University Park, PA (US)

(72) Inventor: Sayed Amin Afzal, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 124 days.

(21) Appl. No.: 16/072,756

(22) PCT Filed: Jan. 26, 2017

(86) PCT No.: PCT/US2017/015058
§ 371 (c)(1),
(2) Date: Jul. 25, 2018

(87) PCT Pub. No.: WO2017/132329
PCT Pub. Date: Aug. 3, 2017

(65) Prior Publication Data
US 2019/0101516 A1  Apr. 4, 2019

Related U.S. Application Data

(60) Provisional application No. 62/287,693, filed on Jan. 27, 2016, provisional application No. 62/287,709, filed on Jan. 27, 2016.

(51) Int. Cl.
*G01N 33/00* (2006.01)
*G01R 33/06* (2006.01)
(Continued)

(52) U.S. Cl.
CPC ........... *G01N 33/0098* (2013.01); *G01B 5/06* (2013.01); *G01B 7/10* (2013.01); *G01N 27/223* (2013.01);
(Continued)

(58) Field of Classification Search
CPC ............. G01N 33/0098; G01N 27/223; G01N 27/226; G01R 33/06; G01R 33/07;
(Continued)

(56) References Cited

U.S. PATENT DOCUMENTS 7,660,698 B1   2/2010  Seelig et al.
2014/0109658 A1*  4/2014  Kah, Jr. ............. G01N 33/0098
                                                              73/73

OTHER PUBLICATIONS

Afzal.A et al. Estimation of Leaf Moisture Content by Measuring the Capacitance, Journal of Agriculture Science and Technology, 2010, vol. 12, pp. 339-346. http://journals.modares.ac.ir/pdf_4575_a4abf0756e97e9ec7e5cb751c7c30e67.html>.
(Continued)

*Primary Examiner* — Vincent Q Nguyen
*Assistant Examiner* — Trung Nguyen
(74) *Attorney, Agent, or Firm* — Dinsmore & Shohl LLP

(57) ABSTRACT

Systems and methods for non-invasively determining a water content, a solute content, and a thickness of plant tissue are disclosed. A system includes a sensing device having a first piece and a second piece, where the first piece and the second piece are coupled together to form a clip. The system further includes a capacitive tissue sensor including a capacitor. The capacitor includes a plurality of coplanar conductive plates. The first piece and the second piece are biased in a closed position to provide a gripping force around the plant tissue such that at least a portion of the plant tissue contacts the plurality of coplanar conductive plates.

19 Claims, 11 Drawing Sheets

(51) Int. Cl.
*G01R 33/07* (2006.01)
*G01B 5/06* (2006.01)
*G01B 7/06* (2006.01)
*G01N 27/22* (2006.01)

(52) U.S. Cl.
CPC .............. *G01R 33/06* (2013.01); *G01R 33/07* (2013.01); *G01R 33/072* (2013.01); *G01B 2210/40* (2013.01); *G01B 2210/58* (2013.01); *G01N 27/226* (2013.01)

(58) Field of Classification Search
CPC .............. G01R 33/072; G01B 2210/40; G01B 2210/58; G01B 7/10; G01B 5/06
USPC .. 324/200, 229–230, 207.13, 219, 500, 529, 324/530
See application file for complete search history.

(56) References Cited

OTHER PUBLICATIONS

Clancy, C. Real answers to real world challenges, Aug. 21, 2015. http://news.psu.edu/story/366981/2015/08/31/research/real-answers-real-world-challenges>.
International Search Report, dated Jun. 2, 2017, International Application No. PCT/US2017/15058, International Filing Date, Jan. 26, 2017.

\* cited by examiner

SENSORS FOR MEASURING WATER/SOLUTE CONTENT AND THICKNESS OF PLANT TISSUE

CROSS-REFERENCE TO RELATED APPLICATIONS

The present application is the U.S. National Stage of PCT/US2017/015058, filed Jan. 26, 2017 and entitled "Sensors for Measuring Water/Solute Content and Thickness of Plant Tissue," which claims priority to U.S. Provisional Patent Application Ser. No. 62/287,693, filed Jan. 27, 2016 and entitled "Capacitive Plant Tissue Sensor" and U.S. Provisional Patent Application Ser. No. 62/287,709, filed Jan. 27, 2016 and entitled "Plant Tissue Thickness Sensor", the contents of each are incorporated herein by reference in their respective entireties.

STATEMENT OF GOVERNMENT SUPPORT

This invention was made with government support under Hatch Act Project No. PEN04425, awarded by the United States Department of Agriculture/NIFA. The Government has certain rights in the invention.

BACKGROUND

Field

The present disclosure relates to devices and methods for measuring water/solute content and/or one or more dimensional aspects of plant tissue, and more particularly, to devices and methods for non-invasively measuring water/solute content to monitor plant status (water/photosynthesis/stomatal conductance status) and determine a stress level (water or environmental stresses, such as light, nutrient, and pest stresses damaging the tissue and decreasing water content and/or photosynthetic activity) that a plant may encounter, and/or devices and methods for non-invasively measuring a thickness of plant tissue. The measurements may be used for research studies, plant water monitoring, irrigation control, to make decisions and apply operations (by management or automatic/manual control) to alleviate the effect of the stress, including, but not limited to, automatic irrigation and light timing.

Technical Background

Measurement of water/solute content in plant tissue may be necessary to ensure that plants are appropriately hydrated and not under environmental stresses, so that watering schedules and amounts can be adjusted accordingly as well as monitoring whether the plants are under environmental stresses that may inhibit photosynthetic and normal activities.

Currently, devices and methods that measure a water/solute content and photosynthetic activity of plant tissue are invasive to the tissue, are based on physiological responses, are not applicable for automatic measurements (thereby labor intensive), are bulky, and/or are inaccurate. For example, some methods require detachment of plant tissue from a plant to calculate the relative water content by weighing the actual, full-turgid, and dry weights of the tissue. In another example, some methods detach plant tissue and apply a pressure bomb to measure water/solute content. Such methods destroy the plant tissue and are not suitable for automatic measurements. In yet another example, water/solute content is indirectly estimated by measuring a leaf property that is related to the water/solute content, such as by measuring leaf thickness and canopy reflectance. However, other interfering factors, such as salinity, ambient temperature, plant species, solar angle, shadowing, illumination, canopy coverage, soil background, atmospheric viewing geometry of the device, leaf thickness, biomass, leaf area index, crop type and development stage, and/or tissue structure may affect the accuracy of such indirect measurements.

One potential solution to these problems is to measure the dielectric constant of the plant tissue to estimate the water/solute content thereof. However, current devices and methods for measuring dielectric constant of the plant tissue are destructive to the tissue, hinder growth of the plant, block light from reaching the plant tissue, prevent transpiration, are bulky and cannot be supported by the plant tissue, and/or do not monitor a single surface of the plant tissue.

Another potential solution to these problems is to measure a dimensional aspect of the plant tissue to determine the water content, as water pressure that develops in plant cells causes the cells to expand. Such expansion can be measured to determine a water content. However, current devices and methods for measuring a dimensional aspect of the plant tissue, such as calipers, micrometers, transducer-based devices, and strain gauge-based devices, are destructive to the tissue, hinder growth of the plant, and are bulky and cannot be supported by the plant tissue. In addition, devices that use a single permanent magnet with high sensitivity magnetic field sensor may result in sensor saturation in instances where the plant tissue is thin.

Accordingly, a need exists for devices and methods for measuring the dielectric constant of plant tissue to determine the water/solute content thereof and/or devices and methods for measuring a dimensional aspect of plant tissue to determine the water content thereof that are non-invasive, do not damage the plant tissue, can be applied without hindering growth of the plant, allow light to pass through to the tissue, allows for transpiration to occur, can be supported by the plant without additional supporting devices, accurately measure thin plant tissue, and/or monitor a single surface of the plant tissue.

SUMMARY

In one embodiment, a system for non-invasively determining one or more of a water content and a solute content in plant tissue includes a sensing device having a first piece and a second piece, where the first piece and the second piece are coupled together to form a clip. The system further includes a capacitive tissue sensor. The capacitive tissue sensor includes a capacitor. The capacitor includes a plurality of coplanar conductive plates. The first piece and the second piece are biased in a closed position to provide a gripping force around the plant tissue such that at least a portion of the plant tissue contacts the plurality of coplanar conductive plates.

In another embodiment, a system for non-invasively determining a dimensional aspect of plant tissue includes a sensing device having a first piece and a second piece, where the first piece and the second piece are coupled together to form a clip. The system further includes a tissue thickness sensor disposed between the first piece and the second piece. The tissue thickness sensor includes a first permanent magnet, a second permanent magnet, and a magnetic sensor. A first magnetic field generated between the first permanent magnet and the second permanent magnet creates a repulsive magnetic force between the first piece and the second piece. A second magnetic field generated by the second permanent magnet reduces an offset magnetic field generated by the first permanent magnet. The magnetic sensor is positioned in a location such that a strength of the magnetic field can be sensed. When the plant tissue is placed between the first piece and the second piece, a change in the strength of the magnetic field is sensed by the magnetic sensor and the dimensional aspect is determined based on the change in the strength.

In yet another embodiment, a system for non-invasively determining one or more of a water content, a solute content, and a thickness of plant tissue includes a sensing device having a first piece and a second piece, where the first piece and the second piece are coupled together to form a clip. The system further includes a capacitive tissue sensor including a capacitor having a plurality of coplanar conductive plates. The first piece and the second piece are biased in a closed position to provide a gripping force around the plant tissue such that at least a portion of the plant tissue contacts the plurality of coplanar conductive plates. The system further includes a tissue thickness sensor disposed between the first piece and the second piece. The tissue thickness sensor includes a first permanent magnet, a second permanent magnet, and a magnetic sensor. A first magnetic field generated between the first permanent magnet and the second permanent magnet creates a repulsive magnetic force between the first piece and the second piece. A second magnetic field generated by the second permanent magnet reduces an offset magnetic field generated by the first permanent magnet. The magnetic sensor is positioned in a location such that a strength of the magnetic field can be sensed. When the plant tissue is placed between the first piece and the second piece, a change in the strength of the magnetic field is sensed by the magnetic sensor and the dimensional aspect is determined based on the change in the strength.

In yet another embodiment, a method for non-invasively determining one or more of a water content and a solute content in plant tissue includes providing a sensing device including a capacitive tissue sensor. The capacitive sensor includes a plurality of coplanar conductive plates. The method further includes placing the sensing device on the plant tissue such that the plurality of coplanar conductive plates contact a surface of the plant tissue, receiving capacitance data from the sensing device, and determining the one or more of the water content and the solute content of the plant tissue from the capacitance data.

In yet another embodiment, a method for non-invasively determining a dimensional aspect of plant tissue includes providing a sensing device including a tissue thickness sensor. The tissue thickness sensor includes a first permanent magnet, a second permanent magnet, and a magnetic sensor. The method further includes placing the sensing device on the plant tissue such that plant tissue is disposed between the first permanent magnet and the second permanent magnet, receiving magnetic field data from the sensing device, where the magnetic field data corresponds to a sensed change in a strength of a magnetic field that is generated between the first permanent magnet and the second permanent magnet due to the plant tissue, and determining the dimensional aspect of the plant tissue from the magnetic field data.

In yet another embodiment, system for non-invasively determining a dimensional aspect of plant tissue includes a sensing device having a first piece and a second piece, where the first piece and the second piece are coupled together to form a clip, and a capacitive tissue thickness sensor disposed between the first piece and the second piece. The capacitive tissue thickness sensor includes a plurality of capacitive plates and a conductive component disposed a distance from the plurality of capacitive plates, the conductive component having a dielectric material. Insertion of the plant tissue between the first piece and the second piece causes the conductive component to move relative to at least one of the plurality of capacitive plates and cause a change in conductivity of at least one of the plurality of capacitive plates. The change in conductivity corresponds to the dimensional aspect of the plant tissue.

These and additional features provided by the embodiments described herein will be more fully understood in view of the following detailed description, in conjunction with the drawings.

BRIEF DESCRIPTION OF DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

DETAILED DESCRIPTION

Figure 1:
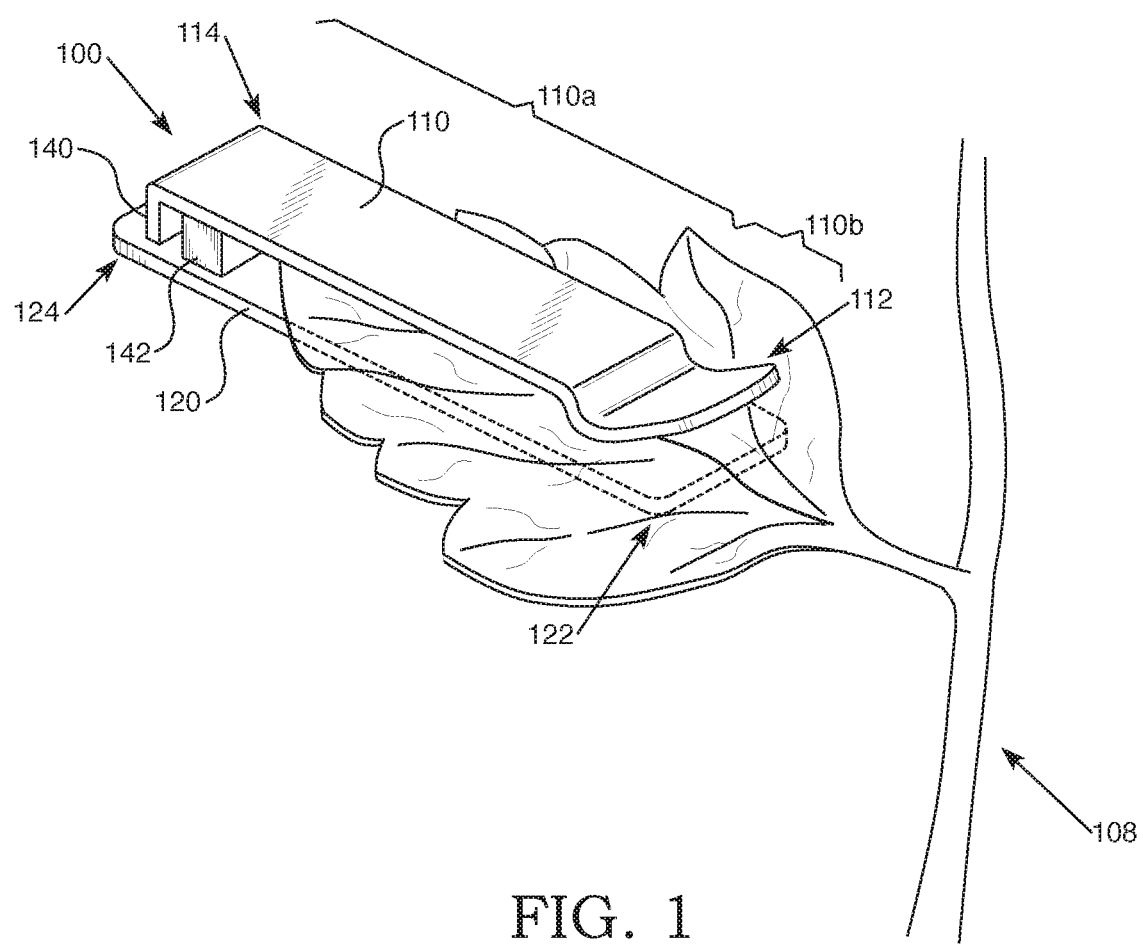
FIG. 1 depicts a side perspective view of an illustrative sensing device placed on plant tissue according to one or more embodiments shown and described herein.

The embodiments described herein are generally related to systems and methods that can be used to non-invasively determine a water/solute content of plant tissue. In some embodiments, the systems and methods may include a capacitive tissue sensor using a dielectric constant of plant tissue to determine the water/solute content of the tissue. The capacitive tissue sensor includes a first piece and a second piece of a clip. A printed circuit board (PCB) is disposed on the first piece. The PCB includes a capacitor with a plurality of coplanar conductive plates. Plant tissue is placed on the coplanar conductive plates of the capacitor such that the tissue sensor grips the tissue with minimum pressure on the tissue and without damaging the tissue. The capacitive tissue sensor is lightweight, small, and grips the plant tissue gently without causing damage. The capacitive tissue sensor may generally be used to measure a dielectric constant of the plant tissue such that a water/solute content of the tissue can be determined and a further determination of whether an adjustment to the amount of water provided to the plant is needed. Such devices, systems, and methods may be particularly useful in applications such as irrigation scheduling, stress monitoring (drought, nutrient, and/or pest stresses), photosynthetic activity monitoring, and/or research studies.

In other embodiments, the systems and methods may include an apparatus that includes a clip device comprising a top portion and a bottom portion. The top portion includes a first magnetic device coupled thereto and the bottom portion includes a second magnetic device coupled thereto. Alternatively, the top portion and the bottom portion may each be magnetically charged. The first magnetic device and the second magnetic device (or alternatively the top portion and the bottom portion) may be arranged such that a magnetic repulsion exists therebetween. That is, the polarity of the respective magnetic device/portion is arranged such that the same poles are facing each other. One or more sensors, such as a Hall-effect sensor, magnetoresistive sensors, or the like, are coupled to the apparatus and generate an output that is proportional to the measured dimensional aspect of the plant tissue, which can be used for research studies, plant water status monitoring, and/or irrigation control.

As used herein, "plant tissue" refers to any tissue of a plant. For example, the plant tissue may be, but is not limited to, a leaf, a stem, a trunk, a fruit, a portion of a flower, a root, and/or the like. In some embodiments, the plant tissue may be live plant tissue. That is, the plant tissue may be tissue that is still attached to a live plant, rather than tissue that has been removed from a live plant and/or tissue from a dead plant.

As used herein, a "dimensional aspect" of plant tissue relates to one or more dimensions of the plant tissue or any portion thereof. For example, the dimensional aspect may refer to a thickness of plant tissue, such as the thickness of a plant leaf.

The capacitive tissue sensor described herein, in addition to being small and lightweight, further operates on a single side of the plant tissue (e.g., on a single side of the plant leaf), which minimizes the size of the capacitive tissue sensor and reduces the rate of capacitance changes in response to water/solute content variations. Moreover, the circuitry contained within the capacitive tissue sensor enables capacitance measurement with fine resolution and low noise gain.

Capacitance is a function of the dielectric constant of the medium and the design and the distance of the capacitive plates. The dielectric constant of a material is dependent on the water and chemical contents of the material, the frequency and the voltage of the measurement, and the temperature. Therefore, the dielectric constant of plant tissue is a function of water content and solute accumulation in the plant tissue. Plant tissue water content may change when the roots of a plant uptake water/solutes and/or when the plant undergoes transpiration.

Photosynthetic activity (photosynthetic products) and osmotic adjustment are the two of the major reasons for solute content changes in plant tissue. Photosynthesis is the main function of plant tissue to provide energy and carbohydrate for the plant functions. Therefore, a decrease in photosynthetic activity results in less photosynthate accumulation and less dielectric constant. Photosynthetic activity can be limited due to one or more factors, such as, but not limited to, insufficient light, water stress, and pests. Therefore, a stress on plant tissue will reduce the photosynthetic activity.

Solute accumulation may also occur as a result of osmotic adjustment. That is, when a water stress tolerant plant is under water tension, it accumulates solutes in the plant tissue to decrease osmotic water potential and absorb more water. The osmotic adjustment also reduces the stomatal conductance to decrease transpiration. Therefore, water stress results in an increase in the plant tissue solute content.

Consequently, water stress can result in either higher or lower dielectric constant, depending on the species of plant. For example, the capacitive tissue sensor described herein has been tested on fava bean plants and tomato plants. When plants were under water stress, the sensor capacitance showed an ascending trend for fava bean plants while this trend was descending for tomato plants. Fava bean plants are more tolerant to water stress due to osmotic adjustment. Therefore, the sensor may show different responses to water stress depending on the crop.

Referring now to the figures, FIG. 1 depicts a schematic view of an illustrative sensing device, generally designated 100, according to various embodiments. The sensing device 100 may be, for example, a clip, a clip-like device, or the like. For example, the sensing device 100 may be generally U-shaped. In various embodiments, the sensing device 100 includes a first piece 110 and a second piece 120. The first piece 110 and the second piece 120 may be coupled together by a hinge 140 in a clip assembly such that the first piece 110 and the second piece 120 can be secured to plant tissue 108, as described in greater detail herein. For example, the first piece 110 and the second piece 120 may be coupled together to form a clip such that the sensing device 100 may clip to a plant leaf whereby the first piece 110 contacts a first surface (e.g., an upper surface) of the plant leaf and the second piece 120 contacts a second surface (e.g., a lower surface) of the plant leaf, with the hinge 140 located beyond a distal portion of the plant leaf.

The first piece 110 may include a distal end 112 and a proximal end 114. The distal end 112 may be spaced a distance from the proximal end 114. Such a distance between the distal end 112 and the proximal end 114 is not limited by this disclosure, and may generally be any distance. In some embodiments, the distance between the distal end 112 and the proximal end 114 may be such that the first piece 110 has a length that is sufficient to support one or more of the various components described herein and/or such that the first piece 110 extends over at least a portion of the plant tissue 108.

Similarly, the second piece 120 may include a distal end 122 and a proximal end 124. The distal end 122 may be spaced a distance from the proximal end 124. Such a distance between the distal end 122 and the proximal end 124 is not limited by this disclosure, and may generally be any distance. In some embodiments, the distance between the distal end 122 and the proximal end 124 may be such that the second piece 120 has a length that is sufficient to support one or more of the various components described herein and/or such that the second piece 120 extends over at least a portion of the plant tissue 108. In some embodiments, the distance between the distal end 112 and the proximal end 114 of the first piece 110 may be substantially equal to the distance between the distal end 122 and the proximal end 124 of the second piece 120. In other embodiments, the distance between the distal end 112 and the proximal end 114 of the first piece 110 may be longer than the distance between the distal end 122 and the proximal end 124 of the second piece 120. In yet other embodiments, the distance between the distal end 112 and the proximal end 114 of the first piece 110 may be shorter than the distance between the distal end 122 and the proximal end 124 of the second piece 120.

In some embodiments, the first piece 110 and/or the second piece 120 may generally be planar such that the first piece 110 and/or the second piece 120 can support one or more components thereon and/or to ensure that particular components contact the plant tissue 108, as described in greater detail herein. In other embodiments, the first piece 110 and/or the second piece 120 may be curved (i.e., not planar) to ensure that particular components contact each other, contact plant tissue, to measure a dimensional aspect (e.g., a thickness) of plant tissue, to measure a capacitance of plant tissue, and/or the like, as described in greater detail herein.

In some embodiments, the first piece 110 and the second piece 120 may be coupled together via the hinge 140. In some embodiments, the hinge 140 may be positioned at the distal end 112 of the first piece 110 and/or the distal end 122 of the second piece 120. In other embodiments, the hinge 140 may be positioned at a location between the distal end 112 and the proximal end 114 of the first piece 110 and/or at a location between the distal end 122 and the proximal end 124 of the second piece 120. In some embodiments, the hinge 140 may bias the first piece 110 and the second piece 120 towards each other. For example, the hinge 140 may bias the distal end 112 of the first piece 110 towards the distal end 122 of the second piece 120. The hinge 140 may provide a biasing force via a spring, such as a torsional spring or the like. However, it will be understood that a biasing force may be provided with any other device or apparatus without departing from the scope of the present disclosure. For example, the hinge 140 may be made of a flexible material that inherently provides a biasing force.

The first piece 110 and the second piece 120 may generally be biased together via the hinge 140 in a closed configuration, whereby the first piece 110 and the second piece 120 contact one another. When a force that counteracts the biasing force is applied to the first piece 110 and/or the second piece 120, the first piece 110 and the second piece 120 may be moved to an open configuration, whereby the first piece 110 and the second piece do not contact one another. For example, if a compressing force that is greater than the biasing force is applied on the proximal ends 114, 124 (i.e., such that the proximal ends 114, 124 are forced toward each other), the distal ends 112, 122 may move away from each other to the open configuration. In another example, an expanding force that is greater than the biasing force, when applied on the distal ends 112, 122, may cause the distal ends 112, 122 to move away from each other to the open configuration.

In some embodiments, the sensing device 100 may further include a stop 142 that minimizes pressure placed on the plant tissue 108 between the first piece 110 and the second piece 120 caused by the biasing force to avoid crushing the plant tissue 108. The stop 142 may generally be located between the first piece 110 and the second piece 120, and between the hinge 140 and the distal ends 112, 122. However, in some embodiments, the stop 142 may be integrated with the hinge 140 so as to prevent the hinge 140 from providing a biasing force past a particular point. In some embodiments, the stop 142 may be a single unit. In other embodiments, the stop 142 may include a first stop portion and a second stop portion, where the first stop portion is disposed on the first piece 110 and the second stop portion is disposed on the second piece 120. In some embodiments, the stop 142 may prevent the first piece 110 and the second piece 120 from moving toward each other past a particular point. In other embodiments, the stop 142 may act as a cushion such that the first piece 110 and the second piece 120 can be brought together by the biasing force, but the stop 142 absorbs some of the pressure caused by the biasing force. In some embodiments, the stop 142 may be made of a shock absorbent material. In some embodiments, the stop 142 may be made of elastic, rubber, silicone, foam, or the like such that the stop 142 exhibits compressible properties. In some embodiments, the stop 142 may be a spring based stop. The stop 142 may generally be sized and shaped such that it can be placed between the first piece 110 and the second piece 120. In some embodiments, the stop 142 may have a thickness that is greater than a distance between the first piece 110 and the second piece 120, but is compressible such that the first piece 110 and the second piece 120 can be touched together by the biasing force exerted by the hinge 140.

In some embodiments, the first piece 110 may be substantially parallel to the second piece 120. In other embodiments, at least a first portion 110a of the first piece 110 may be substantially parallel to the second piece 120. In some embodiments, a second portion 110b of the first piece 110 may be located at or near the distal end 112 of the first piece 110. The second portion 110b may further be angled such that the second portion 110b extends toward the second piece 120 such that the distal end 112 of the first piece 110 contacts the distal end 122 of the second piece 120 and/or causes a compressing force on the plant tissue 108 placed between the first piece 110 and the second piece 120. In other embodiments, the second portion 110b of the first piece 110 may be angled toward the second piece 120 such that the distal end 112 of the first piece 110 is spaced closer to the distal end 122 of the first piece 110, relative to the spacing between the respective proximal ends 114, 124 of the first piece 110 and the second piece 120, while avoiding contact between the distal end 112 of the first piece 110 and the distal end 122 of the second piece 120. However, in such a configuration, when the plant tissue 108 is inserted between the first piece 110 and the second piece 120, a compressing force is placed on the plant tissue 108. Accordingly, the sensing device 100 may grip the plant tissue 108 and retain the plant tissue 108 between the first piece 110 and the second piece 120. As depicted in FIG. 1, in some embodiments, the second portion 110b of the first piece 110 may be curved (i.e., not planar) such that the distal end 112 of the first piece 110 is angled toward the second piece 120 when the sensing device 100 is arranged as described herein. Accordingly, the curvature of the second portion 110b of the first piece 110 may achieve a necessary compressing force on the plant tissue 108.

One or more portions of the sensing device 100 may be constructed of a clear, flexible material. For example, the first piece 110 and/or the second piece 120 may each, respectively, be constructed of the clear, flexible material. The clear, flexible material may generally be any material that allows at least some electromagnetic radiation to pass therethrough. The type of electromagnetic radiation is not limited by this disclosure, and may generally be any type of electromagnetic radiation, including electromagnetic radiation having a wavelength ranging from infrared radiation to ultraviolet radiation, particularly electromagnetic radiation that is generally recognized as consumable by plants (e.g., light that is used as an energy source). For example, a suitable material may allow the passage of visible light therethrough such that the plant tissue to which the material is attached is still able to receive light. Thus, the material does not block light from passing through to the plant tissue. Particular clear and flexible materials are not limited by this disclosure, and may generally be any clear or flexible materials now known or later developed. In some embodiments, the clear, flexible material may be a polymeric material such as, for example, a polycarbonate, ethylene vinyl acetate (EVA), polyvinylchloride (PVC), an acrylate polymer, poly(methyl methacrylate) (PMMA), and polyethylene terephthalate (PETG). In some embodiments, the clear, flexible material may be a resin. Other clear, flexible materials should generally be understood and are included within the scope of the present application.

In some embodiments, one or more portions of the sensing device 100 may be particularly constructed to allow moisture from the plant tissue to evaporate/transpire. In a nonlimiting example, one or more portions of the sensing device 100 may be constructed of a porous material, a material having one or more apertures therethrough, and/or the like. In another nonlimiting example, one or more portions of the sensing device 100 may be constructed of a porous material that can absorb vapor/moisture.

In some embodiments, one or more portions of the sensing device 100 may be constructed of other materials such as, for example, metal, plastic (solid, opaque or transparent), or wood. That is, in some embodiments, the first piece 110 and/or the second piece 120 may be made of the one or more other materials.

In some embodiments, the first piece 110 and/or the second piece 120 may include additional mounting materials or components thereon for affixing the sensing device 100 to the plant tissue 108. Nonlimiting examples of additional mounting materials or components include adhesives, magnets, and/or the like. For example, the sensing device 100 may be secured to the plant tissue 108 by applying an adhesive to the plant tissue 108 and/or one or more portions of the sensing device 100.

Figure 2:
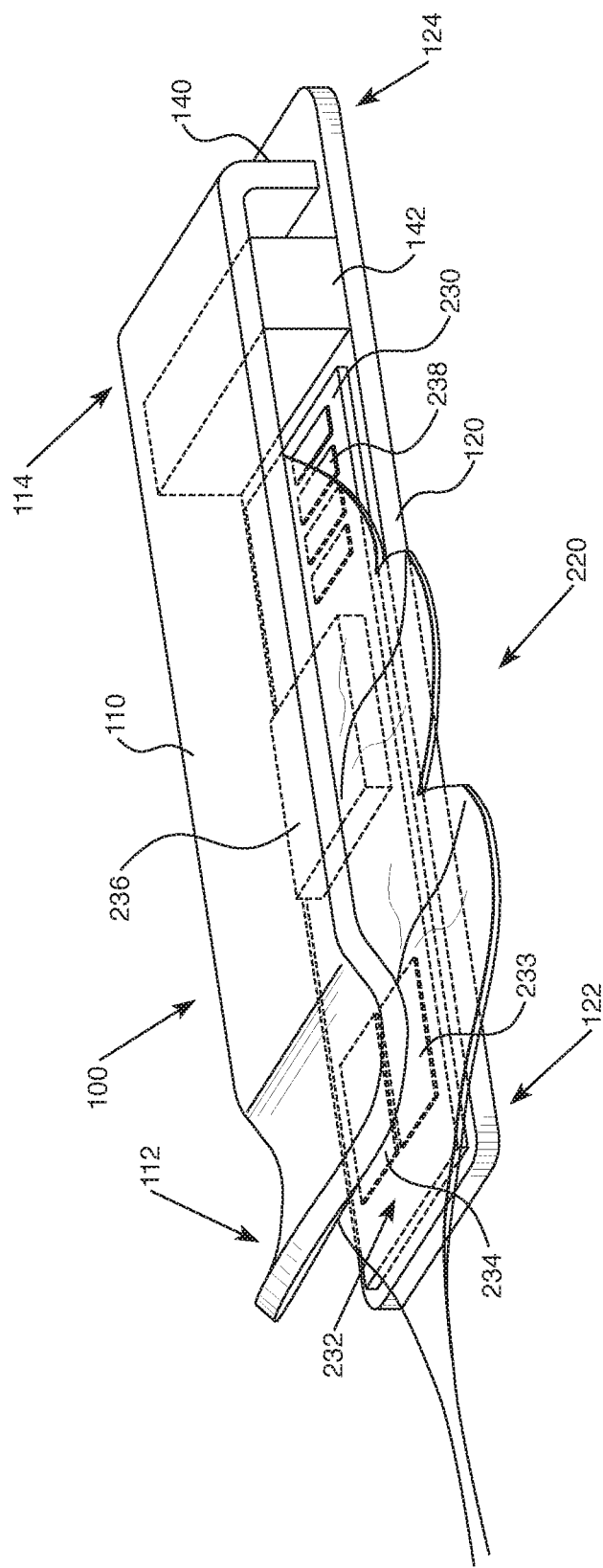
FIG. 2 depicts a side perspective view of an illustrative sensing device including a capacitive tissue sensor according to one or more embodiments shown and described herein.

FIG. 2 depicts an embodiment of the sensing device 100 including a capacitive tissue sensor 220. The capacitive tissue sensor 220 may include various components for measuring a water and/or a solute content of the plant tissue 108 according to one or more embodiments. The capacitive tissue sensor 220 may include a printed circuit board (PCB) 230 disposed on a surface of the second piece 120. In some embodiments, the PCB 230 may be attached to the second piece 120. In other embodiments, the PCB 230 may be integrated with the second piece 120. In yet other embodiments, the PCB 230 may be the second piece 120 (i.e., the second piece 120 is constructed of a PCB material). In some embodiments, the PCB 230 may be constructed of a transparent, flexible, and/or porous material so as to allow electromagnetic radiation to pass therethrough and/or to allow transpiration when the sensing device 100 is attached to plant tissue. In some embodiments, the PCB 230 may be a standard printed circuit board constructed of standard circuit board components, as such components are generally understood. The PCB 230 may extend a particular length along the second piece 120 such that various other components of the capacitive tissue sensor 220 are adjacent to the plant tissue 108 for the purposes of measuring a water and/or a solute content, as described in greater detail herein.

In various embodiments, the capacitive tissue sensor 220 may further include a capacitor 232 having a plurality of conductive plates 233, 234, measuring circuitry 236, and/or an output terminal 238 disposed on or integrated with the PCB 230. The capacitor 232 may generally be any capacitor now known or later developed. For example, in some embodiments, the capacitor 232 may be a coplanar capacitor in which the conductive plates 233, 234 are metallic and parallel relative to one another. It is contemplated that the capacitor 232 may further include additional components not specifically described herein.

Various components of the capacitive tissue sensor 220, including the conductive plates 233, 234, the measuring circuitry 236, and/or the output terminal 238 may be communicatively coupled to one another, such as, for example, via electronic circuitry on the PCB 230 that extends between the conductive plates 233, 234, the measuring circuitry 236, and the output terminal 238. Such a communicative coupling may generally allow one or more signals to be transmitted between any two of the conductive plates 233, 234, the measuring circuitry 236, and the output terminal 238. In addition, the conductive plates 233, 234, the measuring circuitry 236, and/or the output terminal 238 may be electrically coupled to one another, such as, for example, via electronic circuitry on the PCB 230 that extends between the conductive plates 233, 234, the measuring circuitry 236, and the output terminal 238.

While FIG. 2 depicts two conductive plates 233, 234, it should generally be understood that any number of conductive plates may be used. Various materials and components that are used for the plurality of conductive plates 233, 234 in a capacitor should generally be understood and are included within the scope of the present disclosure. For example, in some embodiments, the conductive plates 233, 234 may be constructed of one or more transparent conductive materials. In another example, the plurality of conductive plates 233, 234 and/or the PCB 230 (or a component thereof) may be constructed of a transparent material, film, and/or the like.

In various embodiments, the plurality of conductive plates 233, 234 may be coplanar. That is, the conductive plates 233, 234 may be located on the same plane (i.e., located on the same surface of the PCB 230 and/or the second piece 120). The coplanar location of the plurality of conductive plates 233, 234 advantageously allows the sensing device 100 to be much smaller in size than alternative sensors that are not coplanar, which results in a lighter structure that is less likely to damage the plant tissue 108 and can be supported by the plant tissue 108 without an additional support structure (e.g., a support column not coupled to the plant tissue 108 and/or the like). In addition, the coplanar location of the plurality of conductive plates 233, 234 only measures capacitance on a single side of the plant tissue 108 (e.g., one side of a plant leaf), thereby reducing the rate of capacitance changes in response to water/solute content variations. As such, the plurality of conductive plates 233, 234 may be positioned at a location on the sensing device 100 such that they contact the plant tissue 108 to be measured. For example, in some embodiments, the plurality of conductive plates 233, 234 may be located at or near the distal end 122 of the second piece 120.

In some embodiments, each of the plurality of conductive plates 233, 234 may be generally rectangular in shape and disposed next to one another on the PCB 230. However, such a shape and arrangement is merely illustrative, and other shapes and/or arrangements are contemplated and included within the scope of the present disclosure.

The measuring circuitry 236 may generally be an integrated circuit that measures the capacitance of the conductive plates 233, 234. In some embodiments, the measuring circuitry 236 may be integrated with the conductive plates 233, 234 as part of the capacitor 232. In some embodiments, the measuring circuitry 236 may further measure a supply voltage, measure an external voltage, and/or measure a temperature. In some embodiments, the measuring circuitry 236 may include one or more magnetic field sensors, such as, for example, Hall-effect sensors and magnetoresistive sensors. In some embodiments, the measuring circuitry 236 may be coupled to a memory (not shown) such that the measuring circuitry 236 executes one or more processes based on processing instructions stored in the memory.

The output terminal 238 may generally be any device or component of the capacitive tissue sensor 220 or a portion thereof (e.g., the PCB 230) that receives information from the various other components of the capacitive tissue sensor 220 (such as the conductive plates 233, 234 and/or the measuring circuitry 236), processes the information, and/or outputs the information to one or more external devices, as described in greater detail herein. As such, in some embodiments, the output terminal 238 may include processing circuitry and/or a communications port. Communications between the output terminal 238 and one or more external devices may use any wireless or wired communications, including, but not limited to, technologies that use Ethernet universal serial bus (USB), Bluetooth, Wi-fi, near-field communication (NFC), cellular connections, and/or the like. In addition, communications between the output terminal 238 and one or more external devices may be via any network, such as the Internet, an intranet, a local area network (LAN), a virtual private network (VPN), and/or the like.

It should generally be understood that the PCB 230 is not limited to the various components described herein. That is, in some embodiments, the PCB 230 may include additional components, including, but not limited to, a power supply (e.g., a battery, solar panel, or the like), a transceiver (wired or wireless), a processor, a non-transitory, processor-readable storage device, a humidity meter, an ammeter, a voltmeter, a multimeter, a thermometer, and/or the like. Accordingly, in some embodiments, the PCB 230 and/or one or more components thereof may further be configured to measure one or more of capacitance, supply voltage, external voltage, temperature, and/or the like. In some embodiments, the PCB 230 may incorporate one or more components for measuring the thickness of the plant tissue placed between the first piece 110 and the second piece 120, as described in greater detail herein.

In some embodiments, a protective material may be disposed on (e.g., may coat) the capacitive tissue sensor 220 and/or various components thereof to protect the capacitive tissue sensor 220 and/or the various components thereof from environmental damage. For example, in some embodiments, the capacitive tissue sensor 220 and/or the various components thereof may be coated with a conformal aerosol solution, which may electrically isolate and/or preserve the capacitive tissue sensor 220 and/or the various components thereof (e.g., the conductive plates 233, 234) from humidity and/or sunlight damage. In some embodiments, the protective material may be an electrical insulator that prevents direct contact of the conductive plates 233, 234 with the plant tissue 108 to eliminate the effect of the conductivity of plant tissue 108 on capacitance measurements, as described in greater detail herein.

Figure 3:
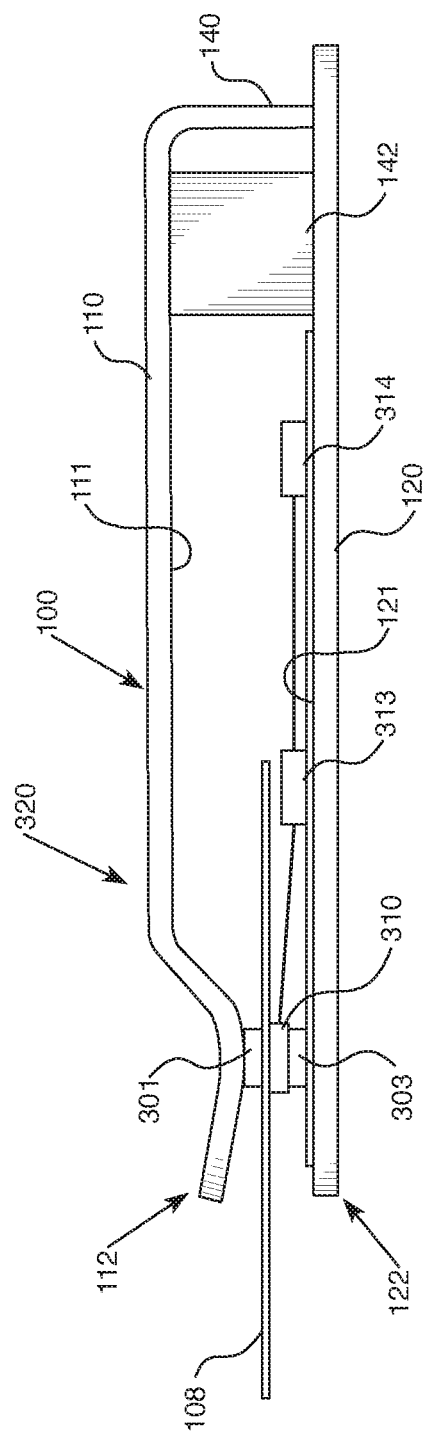
FIG. 3 depicts a side view of an illustrative sensing device including a tissue thickness sensor having vertically arranged components according to one or more embodiments shown and described herein.

FIG. 3 depicts another embodiment of the sensing device 100 including a tissue thickness sensor 320. In some embodiments, the tissue thickness sensor 320 may include a first permanent magnet 301, a magnetic sensor 310, and a second permanent magnet 303 coupled to various portions of the sensing device 100, such as the first piece 110 and/or the second piece 120. In other embodiments, the sensing device 100 may be constructed or partially constructed of materials that exhibit magnetic properties in lieu of the first permanent magnet 301 and/or the second permanent magnet 303. For example, the first piece 110 and/or the second piece 120 may be constructed or partially constructed of a material exhibiting magnetic properties, such as iron, nickel, cobalt, and/or various alloys of any of the foregoing.

The first permanent magnet 301 and the second permanent magnet 303 are not limited by this disclosure, and may generally be any type of magnet, particularly components exhibiting ferromagnetic properties. In some embodiments, the first permanent magnet 301 may be a variable distance (VD) magnet. In some embodiments, the second permanent magnet 303 may be a bias permanent magnet.

The first permanent magnet 301 and the second permanent magnet 303 may each generally be positioned at any location on the sensing device 100, particularly locations that allow placement of the plant tissue adjacent to the first permanent magnet 301 and/or the second permanent magnet 303. For example, in various embodiments, the first permanent magnet 301 may be coupled to the first piece 110 and the second permanent magnet 303 may be coupled to the second piece 120. In some embodiments, the first permanent magnet 301 may be coupled to the sensing device 100 such that the first permanent magnet 301 is positioned on an inside surface 111 of the first piece 110 such that the first permanent magnet 301 faces the second piece 120. Similarly, the second permanent magnet 303 may be coupled to the sensing device 100 such that the second permanent magnet 303 is positioned on an inside surface 121 of the second piece 120 such that the second permanent magnet 303 faces the first piece 110.

Figure 4A:
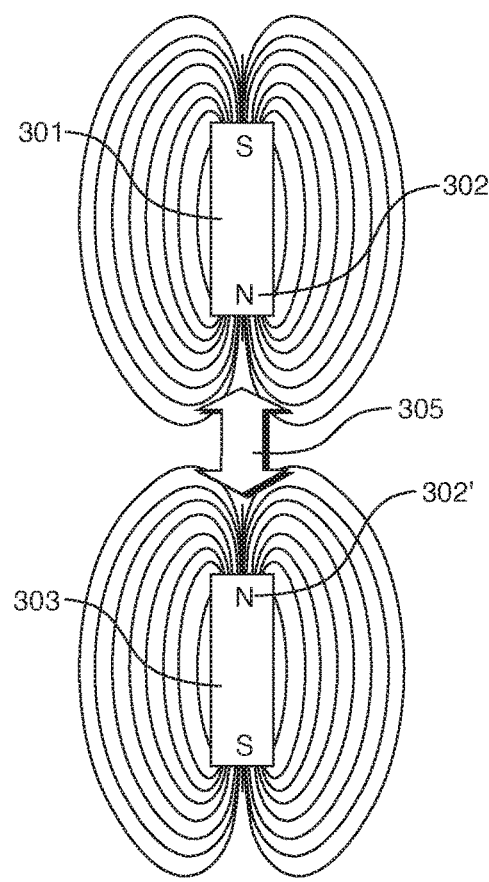
FIG. 4 depicts a schematic view of illustrative magnet placement according to one or more embodiments shown and described herein.
Figure 4B:
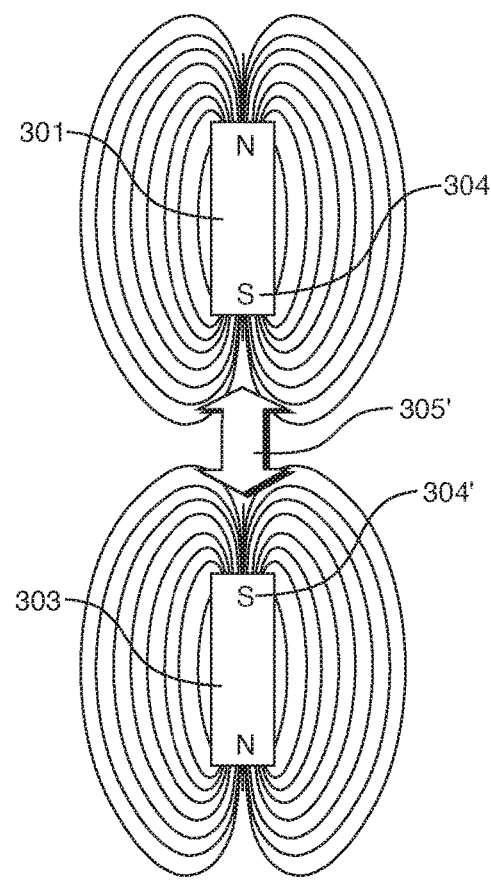

The first permanent magnet 301 and the second permanent magnet 303 may further be positioned on the sensing device 100 such that the respective polarities of the magnets are facing in opposing directions so that the first permanent magnet 301 and the second permanent magnet 303 repel one other. For example, as shown in FIG. 4A, the first permanent magnet 301 and the second permanent magnet 303 may be arranged such that the respective north poles 302, 302' thereof are facing each other, thereby causing a repulsive force (as indicated by the arrow 305). In another example, as shown in FIG. 4B, the first permanent magnet 301 and the second permanent magnet 303 may be arranged such that the respective south poles 304, 304' thereof are facing each other, thereby causing a repulsive force (as indicated by the arrow 305').

Referring again to FIG. 3, the magnetic repulsion that exists due to the positioning of the first permanent magnet 301 and the second permanent magnet 303 may advantageously provide a counteracting force to the biasing force previously described herein because the magnetic repulsion may cause a spreading force between the distal end 112 of the first piece 110 and the distal end 122 of the second piece 120. Such a counteracting force may reduce the amount of pressure placed on the plant tissue 108 when the plant tissue 108 is placed between the first piece 110 and the second piece 120, as described in greater detail herein.

The magnetic sensor 310 may generally be any sensor, magnetometer, or the like that can be used to measure various properties of a magnetic field. For example, in some embodiments, the magnetic sensor 310 may be a Hall-effect sensor. As is generally understood, a Hall-effect sensor is a semiconductor device through which a current may be passed. When the Hall-effect sensor is placed in a magnetic field normal to the current path, a voltage appears across the sensor along an axis that is normal to both the current flow and the magnetic field. In some embodiments, the Hall-effect sensor may be a low sensitivity-type sensor. Such a low sensitivity-type sensor may provide an advantage over systems using a high sensitivity-type Hall-effect sensor because a low sensitivity-type sensor is able to sense thinner tissue than a high sensitivity-type sensor. A very close distance between the first permanent magnet 301 and the Hall-effect sensor applies a high magnetic field on the Hall-effect sensor that may saturate the sensor if it is a high sensitivity-type. On the other hand, a high sensitivity sensor may provide a higher precision in thickness measurement compared to a low sensitivity sensor. Therefore, high or low sensitivity for a Hall-effect sensor is a trade-off between the precision and the range of thickness measurement (range of sensitivity). In other embodiments, the magnetic sensor 310 may be a magnetoresistive sensor. As is generally understood, a magnetoresistive sensor is any sensor that makes use of a magnetoresistive effect, which is a property of a current carrying magnetic material to change its resistance in the presence of an external magnetic field. For example, the electrical resistance of certain ferromagnetic alloys, such as Permalloy or the like, is influenced by external magnetic fields.

In various embodiments, the magnetic sensor 310 may generally be positioned at a location adjacent to the first permanent magnet 301 and/or the second permanent magnet 303. In some embodiments, the magnetic sensor 310 may be positioned between the first permanent magnet 301 and the second permanent magnet 303. In some embodiments, the magnetic sensor 310 may be coupled to the second permanent magnet 303 such that it is located between the second permanent magnet 303 and the first permanent magnet 301. In some embodiments, the first permanent magnet 301, the second permanent magnet 303, and the magnetic sensor 310 may be arranged such that the magnetic sensor 310 is physically coupled to the second permanent magnet 303 and a space is maintained between the magnetic sensor 310 and the first permanent magnet 301. In some embodiments, the space maintained between the magnetic sensor 310 and the first permanent magnet 301 may be such that the plant tissue 108 can be placed between the magnetic sensor 310 and the first permanent magnet 301, as described in greater detail herein. A size of the space between the magnetic sensor 310 and the first permanent magnet 301 is not limited by this disclosure, and may generally be any size space. In some embodiments, a distance between the magnetic sensor 310 and the first permanent magnet 301 (i.e., a width of the space) may be variable. In some embodiments, the magnetic sensor 310 may be positioned such that a sensitive core portion of the magnetic sensor 310 is closer to the first permanent magnet 301 than the second permanent magnet 303 such that the magnetic sensor 310 produces a higher rate of output voltage variations in response to a dimensional aspect change of the tissue.

When the first permanent magnet 301 is at its closest distance to the magnetic sensor 310, the first permanent magnet 301 may apply a particular amount of magnetic field strength on the magnetic sensor 310 as an offset magnetic field strength, which is reduced by distancing the first permanent magnet 301 from the magnetic sensor 310. Therefore, the high magnetic field at close distances may saturate the magnetic sensor 310, which means the magnetic sensor 310 may not be sensitive for very thin tissue thicknesses if the magnetic sensor 310 is a high sensitivity-type. In addition to the repulsion force described herein, the second permanent magnet 303 aligned with reverse polarity to the first permanent magnet 301 may help to reduce the offset magnetic field strength, which may avoid magnetic sensor saturation for thin tissue thicknesses. The first permanent magnet 301 and the second permanent magnet 303 would thus be aligned vertically. However, in other embodiments, the arrangement of the first permanent magnet 301 and the second permanent magnet 303 may differ from vertical alignment and/or be one or more first permanent magnets 301 and/or one or more second permanent magnets 303.

In embodiments where the magnetic sensor 310 is a Hall-effect sensor, the magnetic sensor 310 may be placed such that it is vertically aligned with the first permanent magnet 301 and the second permanent magnet 303, as depicted in FIG. 3. However, the arrangement of the first permanent magnet 301, the magnetic sensor 310, and the second permanent magnet 303 can be aligned non-vertically, as shown and described herein, for example, with respect to FIGS. 5 and 7B.

In embodiments where the magnetic sensor 310 is a magnetoresistive sensor, the magnetic sensor 310 need not be placed such that it is vertically aligned with the first permanent magnet 301 and the second permanent magnet 303 to ensure appropriate operation. However, it should be understood that in embodiments where the magnetic sensor 310 is a magnetoresistive sensor, it may be placed in vertical alignment with the first permanent magnet 301 and the second permanent magnet 303 or may be placed in an alternative arrangement, such as the arrangement of components as depicted and described herein with respect to FIGS. 5, 6A, 6B, 7A, and 7B. Use of a magnetoresistive sensor may allow for detection of smaller changes in the magnetic field produced by the first permanent magnet 301 and/or the second permanent magnet 303 than the Hall-effect sensor, which may allow for a greater accuracy in determining a dimensional aspect of the plant tissue.

In various embodiments, the tissue thickness sensor 320 may also include a temperature sensor 313 and/or a supply voltage sensor 314. The temperature sensor 313 may be positioned at any location on the sensing device 100. As such, the location of the temperature sensor 313 is not limited by this disclosure. In some embodiments, the temperature sensor 313 may be positioned at a location that is suitable to measure a temperature of the plant tissue 108 when the sensing device 100 is clipped onto the plant tissue 108, as described in greater detail herein. The temperature sensor 313 may further be communicatively coupled to one or more components of the tissue thickness sensor 320 and/or one or more external components, as described in greater detail herein. The supply voltage sensor 314 may also be positioned at any location on the sensing device 100. As such, the location of the supply voltage sensor 314 is not limited by this disclosure. The supply voltage sensor 314 may be communicatively coupled, electrically coupled, and/or physically coupled to one or more components of the tissue thickness sensor.

As should be generally understood, the temperature sensor 313 may measure a temperature of the plant tissue 108 when the sensing device 100 is attached to the plant tissue 108 and/or may measure ambient temperature. Such a temperature may be further used to determine various properties of the plant tissue, as described in greater detail herein.

The supply voltage sensor 314 may generally measure an amount of voltage that is supplied to the tissue thickness sensor 320. As such, the temperature sensor 113 and/or the supply voltage sensor 314 may be communicatively or physically coupled to the tissue thickness sensor 320. In some embodiments, the temperature sensor 313 and/or supply voltage sensor 314 may be used to calibrate the tissue thickness sensor 320.

Figure 5:
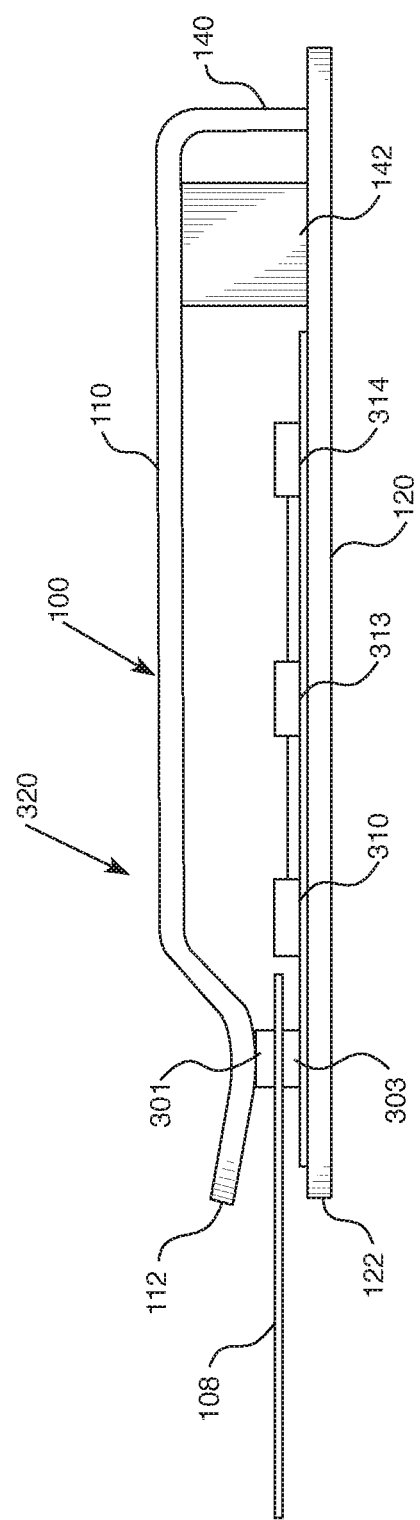
FIG. 5 depicts a side view of an illustrative sensing device including a tissue thickness sensor having non-vertically arranged components according to one or more embodiments shown and described herein.

FIG. 5 depicts an alternative configuration of the sensing device 100 having a tissue thickness sensor 320 according to an embodiment. As shown in FIG. 5, the magnetic sensor 310 is not vertically aligned with the first permanent magnet 301 or the second permanent magnet 303. Rather, the magnetic sensor 310 is placed at another location on the sensing device 100 with respect to the first permanent magnet 301 and/or the second permanent magnet 303. The other location of the magnetic sensor 310 is not limited by this disclosure and may generally be any location that still allows for appropriate functioning of the magnetic sensor 310 as described herein. For example, in some embodiments, the magnetic sensor 310 may be placed adjacent to the second permanent magnet 303 on the second piece 120. Such a configuration as shown in FIG. 5 is specific to embodiments where the magnetic sensor 310 is a magnetoresistive sensor.

Figure 6A:
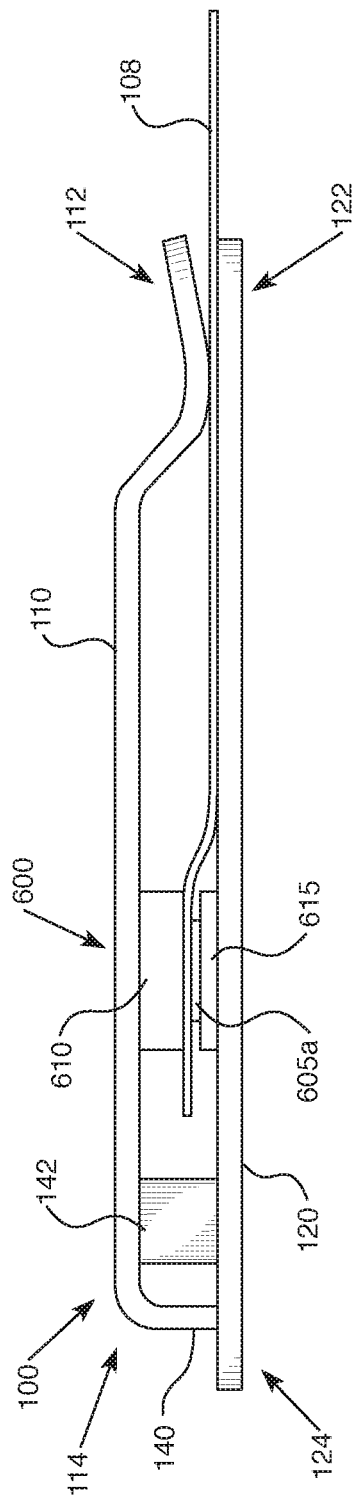
FIG. 6A depicts a side view of an illustrative sensing device including a capacitive tissue thickness sensor according to one or more embodiments shown and described herein.
Figure 6B:
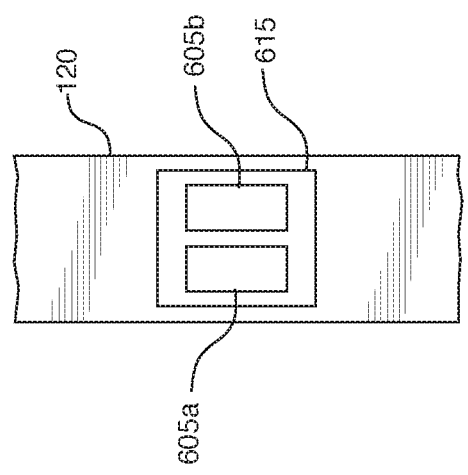
FIG. 6B depicts a cut-away top view of the sensing device of FIG. 6A according to one or more embodiments shown and described herein.

FIGS. 6A-6B depict an alternative configuration of the sensing device 100 having a capacitive tissue thickness sensor 600 according to an embodiment. The capacitive tissue thickness sensor 600 may generally include a plurality of capacitive plates 605a, 605b (collectively 605) and a conductive component 610. The plurality of capacitive plates 605 may be located on a first portion of the sensing device 100 and the conductive component 610 may be located in a corresponding second portion of the sensing device 100 such that the plurality of capacitive plates 605 and the conductive component are arranged such that they are vertically aligned. For example, the plurality of capacitive plates 605 may be located on the second piece 120 and the conductive component may be located on the first piece 110. The horizontal location of the plurality of capacitive plates 605 and the conductive component 610 relative to the respective distal ends 112, 122 of the first piece 110 and the second piece 120 and/or the respective proximal ends 114, 124 of the first piece 110 and the second piece 120 is not limited by the present disclosure. That is, the plurality of capacitive plates 605 and the conductive component 610 may be positioned at any location between the respective distal ends 112, 122 of the first piece 110 and the second piece 120 and the respective proximal ends 114, 124 of the first piece 110 and the second piece 120.

The plurality of capacitive plates 605 may be spaced a distance apart from the conductive component 610 such that a gap exists between the plurality of capacitive plates 605 and the conductive component 610. Such a gap may be sized such that the plant tissue 108 can be inserted therebetween. However, it should be understood that the plant tissue 108 need not necessarily be placed between the capacitive plates 605 and the conductive component 610 in order to measure a thickness. For example, in some embodiments, the plant tissue 108 may be located between the first piece 110 and the second piece 120, but not between the capacitive plates 605 and the conductive component 610. To maintain a particular gap size, the capacitive tissue thickness sensor may further include a spacing component 615 that is located between the plurality of capacitive plates 605 and the second piece 120 in some embodiments.

Each of the plurality of capacitive plates 605 may be positioned in a coplanar arrangement with respect to one another. That is, a first capacitive plate 605a and a second capacitive plate 605b may be located on the same plane (i.e., located on the same surface of the spacing component 615 and/or the second piece 120), as shown in FIG. 6B. The coplanar location of the plurality of capacitive plates 605 advantageously allows the sensing device 100 to be much smaller in size than alternative sensors that are not coplanar, which results in a lighter structure that is less likely to damage the plant tissue 108 and can be supported by the plant tissue 108 without an additional support structure (e.g., a support column not coupled to the plant tissue 108 and/or the like).

Figure 7A:
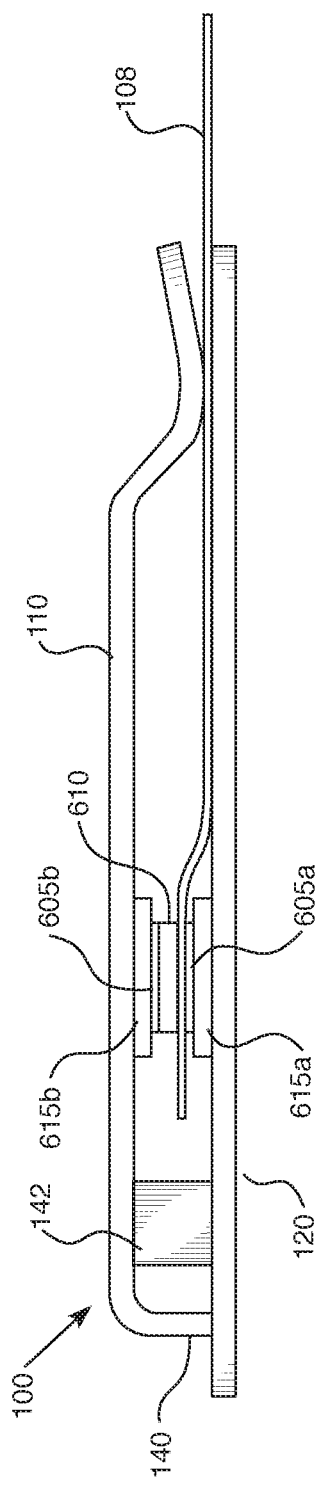
FIG. 7A depicts a side view of an illustrative sensing device including another capacitive tissue thickness sensor according to one or more embodiments shown and described herein.

The configuration depicted in FIGS. 6A and 6B is merely illustrative, and other configurations for the capacitive tissue thickness sensor 600 may also be used without departing from the scope of the present disclosure. For example, as depicted in FIG. 7A, the capacitive tissue thickness sensor 600 may include the first capacitive plate 605a disposed on a different portion of the sensing device 100 than the second capacitive plate 605b. More specifically, the first capacitive plate 605a may be disposed on the first piece 110 (or alternatively on a first spacing component 615a) and the second capacitive plate 605b may be disposed on the second piece 120 (or alternatively on a second spacing component 615b). In addition, the conductive component 610 may be disposed on the first capacitive plate 605a such that a gap exists between the conductive component 610 and the second capacitive plate 605b. Similar to the scenario described above, the plant tissue 108 may be inserted within the gap between the conductive component 610 and the second capacitive plate 605b (or between the first piece 110 and the second piece, but outside of the gay between the conductive component 610 and the second capacitive plate 605b). In such a configuration, the conductive component 610 may be arranged between the first capacitive plate 605a and the second capacitive plate 605b in a vertical configuration.

Figure 7B:
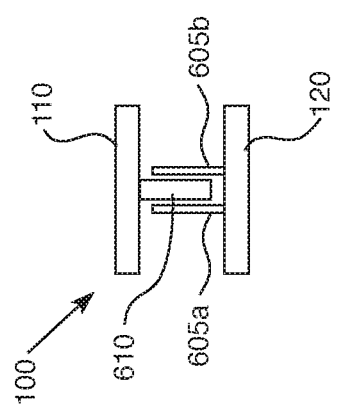
FIG. 7B depicts a front view of an illustrative sensing device including yet another capacitive tissue thickness sensor according to one or more embodiments shown and described herein.

In another example, as depicted in FIG. 7B, the conductive component 610 may be positioned between the first capacitive plate 605a and the second capacitive plate 605b in a horizontal configuration. More specifically, the conductive component 610 may be disposed on the first piece 110 and the capacitive plates 605a, 605b may be disposed on the second piece 120 such that the first capacitive plate 605a is located distally from the conductive component 610 and the second capacitive plate 605b is located proximally from the conductive component 610. The various components may be positioned such that gaps exists between the first capacitive plate 605a, the conductive component 610, and the second capacitive plate 605b. As such, the conductive component 610 may move between the first capacitive plate 605a and the second capacitive plate 605b In each of the embodiments depicted in FIGS. 6A-6B and 7A-7B, the capacitive plates 605 may generally be any type of parallel plates that are used for the purposes of measuring capacitance, and are otherwise not limited by the present disclosure. The conductive component 610 may be, for example, a dielectric material, particularly a material having a high-dielectric constant, including super dielectric materials. Illustrative materials that may be used for the conductive component 610 include, but are not limited to, strontium titanate, hafnium silicate, zirconium silicate, hafnium dioxide, and zirconium dioxide. The conductive component 610 may be moveable relative to the capacitive plates 605 such that the conductive component 610 causes changes in an electrical capacitance of the capacitive plates 605 as described herein. More specifically, as shown in FIGS. 6A-6B, the conductive component 610 may move due to a change in the thickness of the plant tissue 108 such that the distance between the conductive component 610 and the capacitive plates 605 varies. That is, the thickness of the plant tissue 108, as it increases or decreases, may expand or contract a distance between the first piece 110 and the second piece 120, which, in turn, expands or contracts a distance between the conductive component and the capacitive plates 605. In FIGS. 7A-7B, a change in the distance between the first piece 110 and the second piece 120 (e.g., due to a change in the thickness of the plant tissue 108) changes the amount of the space between the first capacitive plate 605a and the second capacitive plate 605b occupied by the conductive component 610. The ability of the conductive component 610 to move relative to the first capacitive plate 605a and the second capacitive plate 605b may be used for the purpose of determining a thickness of the material causing the conductive component 610 to move (e.g., the thickness of the plant tissue 108).

Figure 8:
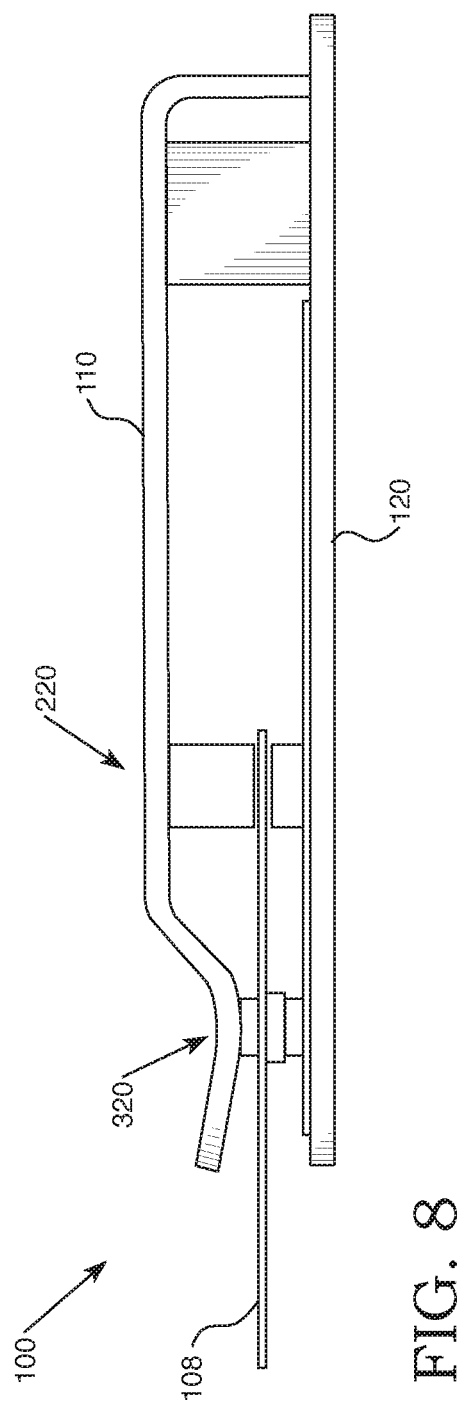
FIG. 8 depicts a side view of an illustrative sensing device including a capacitive tissue sensor and a tissue thickness sensor according to one or more embodiments shown and described herein.

FIG. 8 depicts another embodiment of the sensing device 100 including the capacitive tissue sensor 220 and the tissue thickness sensor 320. While FIG. 8 depicts the tissue thickness sensor 320 specifically described with respect to FIGS. 3 and 5, it should be understood that the sensing device 100 depicted in FIG. 8 may incorporate any variation of the tissue thickness sensor, including the capacitive tissue thickness sensor 600 described with respect to FIGS. 6A-6B and 7A-7B. The various sensors may be disposed on various portions of the sensing device 100 with respect to one another, and are otherwise not limited by the present disclosure. In embodiments where the sensing device includes the capacitive tissue sensor 220 and the tissue thickness sensor 320 (or alternatively the capacitive tissue thickness sensor 600), the sensing device may be particularly configured to measure both a thickness of the plant tissue 108 and a water/solute content of the plant tissue 108 at substantially the same time without the need for separate sensing devices.

To ensure that the capacitive tissue sensor 220 and the tissue thickness sensor 320 do not interfere with one another when combined on the same sensing device 100, it may be necessary to isolate the sensors, while still allowing access to the plant tissue 108. As such, an isolating material may be placed between the capacitive tissue sensor 220 and the tissue thickness sensor 320. In some embodiments, the isolating material may be a coating, a cover, or the like that is deposited on or caused to surround the capacitive tissue sensor 220 and/or the tissue thickness sensor 320. For example, in some embodiments, the capacitive tissue sensor 220 and/or the tissue thickness sensor 320 may be coated with an aerosol conformal coating.

Figure 9:
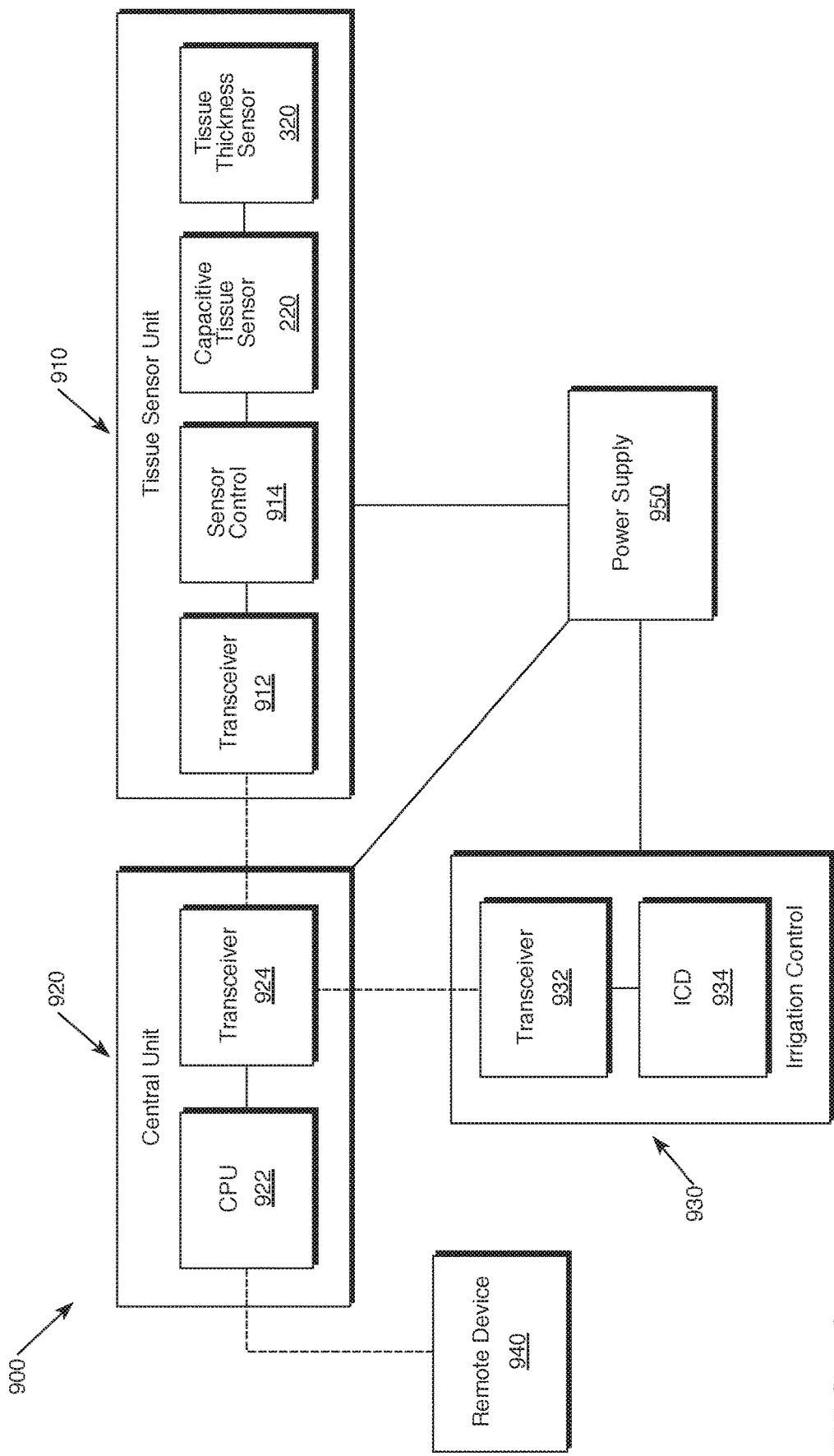
FIG. 9 depicts a block diagram of an illustrative control system for controlling a sensing device according to one or more embodiments shown and described herein.

In order to adequately monitor a thickness of plant tissue and/or a water/solute content of plant tissue for the purposes of appropriately irrigating plants, the various sensors described herein may each be communicatively coupled to a control system 900, as depicted in FIG. 9. It should be understood that the design/arrangement of the control system 900 described herein is merely illustrative, and other designs/arrangements are contemplated. For example, each component may directly communicate with a central device. In another example, the system may incorporate one or more access points that relay communication. In yet another example, one or more sensor units may further act as access points for relaying communications.

As shown in FIG. 9, the control system 900 may generally include a tissue sensor unit 910, a central unit 920, and an irrigation control unit 930. In some embodiments, the control system 900 may further include a remote device 940. Also, in some embodiments, the control system 900 may include a power supply 950.

As shown by the dashed lines, the tissue sensor unit 910, the irrigation control unit 930, and the remote device 940 may each be communicatively coupled to the central unit 920. Communications between the various components may be via any wireless or wired communications, including, but not limited to, technologies that use Ethernet, universal serial bus (USB), Bluetooth, Wi-Fi, near-field communication (NFC), cellular connections, and/or the like. In addition, communications between the various components may be over any network, such as the Internet, an intranet, a local area network (LAN), a virtual private network (VPN), and/or the like.

As shown by the solid lines, the tissue sensor unit 910, the central unit 920, and/or the irrigation control unit 930 may each be electrically connected to the power supply 950. While only a single tissue sensor unit 910 is depicted, it should be understood that the system may include a plurality of tissue sensor units 910 without departing from the scope of the present disclosure. Similarly, while only a single irrigation control unit 930 and a single remote device 940 are depicted, it should be understood that the control system 900 may include a plurality of irrigation control units 930 and/or a plurality of remote devices 940 without departing from the scope of the present disclosure.

The tissue sensor unit 910 may generally include the capacitive tissue sensor 220 and/or the tissue thickness sensor 320 (or the capacitive tissue thickness sensor 600) described herein with respect to FIGS. 1-8. In addition, the tissue sensor unit 910 may also include a sensor control device 914, which may be a processing device or the like that transmits signals for controlling the capacitive tissue sensor 220 and/or the tissue thickness sensor 320 (or the capacitive tissue thickness sensor 600). In some embodiments, the sensor control device 914 may receive signals from the capacitive tissue sensor 220 and/or the tissue thickness sensor 320 (or the capacitive tissue thickness sensor 600). In some embodiments, the sensor control device 914 may be coupled to, incorporated with, or a portion of one or more of the components previously described herein, such as, for example, the measuring circuitry 236 (FIG. 2). In some embodiments, the tissue sensor unit 910 may further include a transceiver 912, which may be any data transmission device now known or later developed. The transceiver 912 may transmit and/or receive signals to/from the central unit 920. In some embodiments, the transceiver 912 may be coupled to, incorporated with, or a portion of one or more of the components previously described herein, such as, for example, the output terminal 238.

The central unit 920, which may also be referred to as a supporting unit, may generally include a processing device 922 and/or a transceiver 924. The processing device 922 may generally be any processing device now known or later developed, such as, for example, a central processing unit (CPU), an integrated circuit, or the like. The processing device 922 may be coupled to a non-transitory, processor-readable memory (not shown) such that the processing device 922 executes one or more processes based on processing instructions stored in the memory. In some embodiments, the processing device 922 may receive one or more instructions from the remote device 940 (e.g., computer, mobile phone, tablet, or the like) and executes one or more processes based on the instructions. In some embodiments, the processing device 922 may function with one or more other components (e.g., a voltage measurement device/circuit or the like) to determine a voltage provided by one or more components of the tissue sensor unit 910, as described in greater detail herein. The transceiver 924 may transmit and/or receive signals to/from the tissue sensor unit 910 and/or a component thereof (or a plurality of tissue sensor units 910 and/or components thereof), the irrigation control unit 930 (or a plurality of irrigation control units 930), and/or the remote device 940.

In some embodiments, the central unit 920 may be a component that is separate from the tissue sensor unit 910, as shown in FIG. 9. However, it should be understood that in other embodiments, the central unit 920 may be physically coupled to or integrated with the tissue sensor unit 910. In embodiments where the control system 900 includes a plurality of tissue sensor units 910 and the central unit 920 is not a standalone unit, the control system 900 may include a plurality of central units 920, each of which is coupled to or integrated with each of the plurality of tissue sensor units 910.

In some embodiments, the central unit 920 may acquire data, store data, calibrate components, analyze data, and display data received from the tissue sensor unit 910, a component thereof, or a plurality of tissue sensor units 910. Thus, the central unit 920 may include one or more peripheral components, such as, for example, one or more input devices (e.g., keyboard, touchscreen, mouse, etc.), one or more display devices, and/or the like for the purpose of displaying the data received from the tissue sensor unit 910 and/or receiving commands. In some embodiments, the central unit 920 may provide remote access to the remote device 940 for the purpose of displaying the data received from the tissue sensor unit 910 and/or receiving commands.

The irrigation control unit 930 may generally include one or more irrigation control devices 934 and one or more transceivers 932. Each of the one or more irrigation control devices 934 may generally be any device or component thereof now known or later developed for supplying water/solute from a water source to at least one plant. Nonlimiting examples of an irrigation control device may include a pump, a valve, a relay a mist sprayer, a humidifier, a fertilizing device, a light source, and/or the like. Other nonlimiting examples may include a solenoid valve, a center pivot irrigation system, a drip irrigation system, a sprinkler irrigation system, and/or the like. The irrigation control unit 930 may be substituted with other types of controllers which the sensor information can be employed for, including, but not limited to, light controllers since the sensor is sensitive to photosynthetic activity and may be used for control of time and intensity of exposed light to improve the photosynthetic activity. In some embodiments, an irrigation control device 934 may be, for example, a solenoid valve controller. Each of the one or more irrigation control devices 934 may generally provide water/solute to a plant based on signals received from the central unit 920, as described in greater detail herein. Each of the one or more transceivers 932 may transmit and/or receive signals to/from the central unit 920 and/or relay control signals to the one or more irrigation control devices 934.

The power supply 950 may generally be any device for providing electrical power to any one of the devices of the system, including, but not limited to, the tissue sensor unit 910, the central unit 920, the irrigation control unit 930, as well as components thereof. For example, the power supply 950 may provide power to the capacitive tissue sensor 220 and/or the tissue thickness sensor 320. While a single power supply 950 is depicted in FIG. 9, the present disclosure is not limited to such. Instead, a plurality of power supplies 950 may be used to individually power the various components described herein. In some embodiments, the power supply 950 may be a standalone unit. In other embodiments, the power supply 950 may be integrated with one or more of the components described herein. Illustrative power supplies include, but are not limited to, batteries, AC/DC convertors, solar cells, power generation motors, and/or the like.

It should generally be understood that various components of the system described with respect to FIG. 9 are optional components. Accordingly, certain components described herein with respect to FIG. 9 may be omitted, replaced, combined, split into sub-components, and/or the like.

In operation, the various components of the systems described herein may be used to determine the capacitance of plant tissue and/or the thickness of the plant tissue, which, in turn, may be used to determine a water/solute content of the plant tissue. Once the water/solute content of the tissue has been determined, a determination may be made as to whether the plant is in need of additional or less watering. While the present disclosure relates primarily to measuring the capacitance and/or thickness of the plant tissue for the purposes of determining water/solute content, other determinations may be made without departing from the scope of the present disclosure. For example, in some embodiments, the capacitance and/or thickness of the plant tissue may be used to determine various photosynthesis properties.

Figure 10:
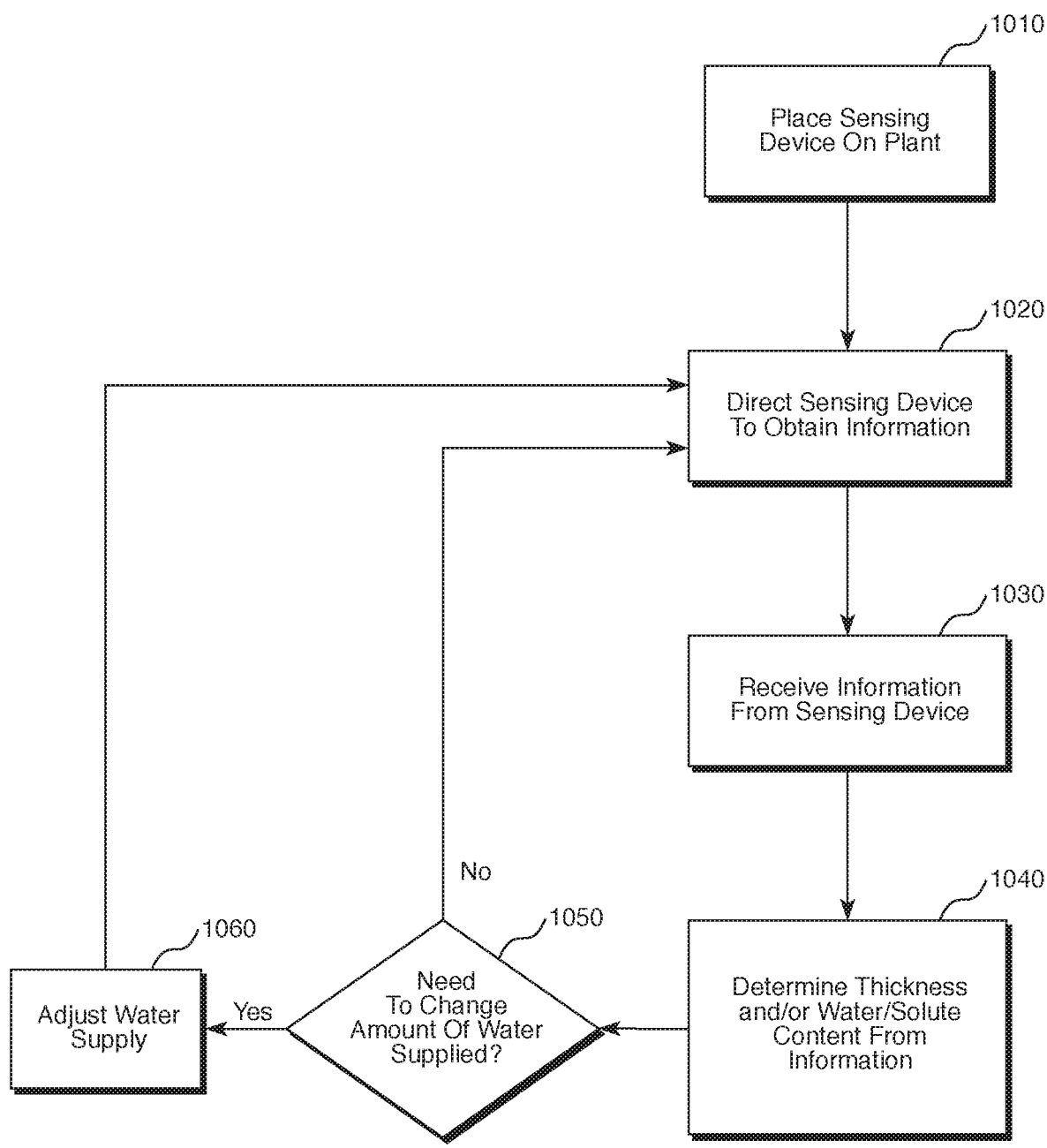
FIG. 10 depicts a flow diagram of an illustrative method of sensing plant tissue using a sensing device according to one or more embodiments shown and described herein.

FIG. 10 depicts a block diagram of an illustrative method of operating a sensing device to determine a water content of a plant according to one or more embodiments. Such a method of determining the water content in a plant may include placing the sensing device on the plant at step 1010. In some embodiments, placing the sensing device on the plant may be accomplished by securing (e.g., clipping) the sensing device to the plant tissue. That is, the sensing device may be placed into an open configuration, placed around the plant tissue, and the hinge is allowed to bias the first piece and the second piece together to secure the sensing device to the plant tissue. The sensing device may generally be secured to any type of plant tissue, particularly plant tissue that would allow for an accurate capacitive reading as described herein. For example, the plant tissue may be, but is not limited to, a leaf, a stem, a trunk, a fruit, a portion of a flower, a root, and/or the like. In some embodiments, the sensing device may be secured to live plant tissue. For example, plant tissue may be tissue that is still attached to a live plant, not tissue that has been removed from a live plant and/or tissue from a dead plant. The sensing device may be placed such that each of the coplanar conductive plates contact the plant tissue such that an electrical signal can be passed between the coplanar conductive plates via the tissue and/or such that the tissue is inserted between the first and second permanent magnets (or between the capacitive plates and the conductive component).

Once the capacitive tissue sensor has been placed on the tissue, the sensing device may be directed to obtain information regarding the plant tissue at step 1020. The information may be received from the sensing device (e.g., received by the central unit) at step 1030 and a thickness and/or water/solute content of the plant tissue may be determined from the received information at step 1040.

In embodiments where a capacitive tissue sensor is used to obtain information from the plant tissue, a capacitive signal may be generated between the coplanar conductive plates. The capacitive signal may generally be understood and is not described in further detail herein. The measuring circuitry may measure the capacitive signal that is passed through the plant tissue via the conductive plates to determine a dielectric constant of the tissue. Determining the dielectric constant may be completed by any method of determination, including, by not limited to, applying a theoretical formula and applying an empirical equation. For example, Gauss' law may be applied to a surface surrounding one of the parallel plates. If the surface is correctly chosen and the fringing flux lines at the edge of the plates are ignored, the total chare $Q$ inside the surface may be equal to the total displacement flux D times the area of the surface, resulting in Equation (1):

$$C = \frac{\varepsilon_0 \varepsilon_r S}{d} = 8.854 \times 10^{-12} \times \frac{\varepsilon_r S}{d} \quad (1)$$

where C is the capacitance in farads, $\varepsilon_0 = 8.854 \times 10^{-12}$, $\varepsilon_r$ is the relative dielectric constant (1 for vacuum), S is the area in square meters, and d is the spacing in meters. In another example, the capacitance of coplanar plates that are surrounded by a ground with $L_1 \gg L_2$ have a mutual capacitance, which is given by Equation (2):

$$C = \frac{\varepsilon_0 \varepsilon_r L_2}{\pi} \ln \frac{(s+b_1)(s+b_2)}{s(s+b_1+b_2)} \quad (2)$$

where $b_1$ and $b_2$ are the widths, respectively of the plates, $L_1$ and $L_2$ are the lengths, respectively, of the plates, and s is the distance between the plates.

Capacitance may be measured in a frequency and a voltage. The frequency and voltage is not limited by this disclosure. For example, the voltage may be about 3 V DC and the frequency may be about 8 Hz that can be considered as DC. In embodiments where a higher frequency is used, impedance may be measured to calculate the capacitance. Illustrative methods of determining capacitance with a higher frequency may include, but are not limited to, methods that are based on time domain reflectometry (TDR), field domain (FD), and relaxation frequency.

The measuring circuitry may further determine the water/solute content of the plant based on the dielectric constant. The water/solute content of the tissue may be determined using one or more calibration equations/curves. The level of the stress on the plant (e.g., water/solute and/or environmental stresses) may be determined by analyzing the dynamics of the capacitance measurements to detect whether plant is in a normal, a moderate stress, or a severe stress state. In some embodiments, the water/solute content may be proportional to the capacitive signal. In such a process (whether determining dielectric constant or processing capacitance), a combination of temperature, supply voltage, and thickness measurements may be used to standardize/calibrate the measurements as the empirical equation/algorithm. Also, the process may be adjusted based on the species, the frequency and the voltage of the measurement, and the specific design of sensor (such as the type of the conformal coating) as the other part of the empirical equation/algorithm.

In embodiments where a tissue thickness sensor is used to obtain information from the plant tissue, a magnetic field may be measured. More specifically, when no object is inserted between the first portion and the second portion (i.e., a dimensional aspect of 0), the magnetic field generated by the first permanent magnet and the second permanent magnet will have a first strength, which is measured by the magnetic sensor. When an object is inserted between the first portion and the second portion (e.g., plant tissue), the magnetic field generated by the first permanent magnet and the second permanent magnet will be altered, and such an altered magnetic field can be measured by the magnetic sensor. In some embodiments, the altered magnetic field will have a second strength. In some embodiments, the second strength may be less than the first strength.

In an embodiment, an absolute reading from the magnetic sensor may be used as an indicator of the thickness of the plant tissue. In another embodiment, the detected difference between the first strength and the second strength can be used to determine the thickness of the plant tissue, which in turn, can be use to determine the amount of water present in the cells of the plant tissue.

A calibration curve can be created to relate the thickness (or relative thickness) and the water/solute content (or relative water/solute content) of a tissue. This calibration curve can be used to determine the plant/tissue water/solute status for different thicknesses of the tissue. In another embodiment, the dynamics of thickness can be used as an indicator of the plant/tissue water/solute status. This approach, the slopes, temporal maximums and minimums, turning points, breakpoints, and/or any other characteristics of the dynamics would be used to determine the plant/tissue water/solute status. One way is to monitor the thickness of a living tissue, such as a leaf attached on the plant, at night, to observe if the tissue/leaf could recoup its thickness as much as the previous night. If the tissue cannot recoup its thickness, such may be an indicative signal of water/solute stress. If the thickness of the tissue/leaf at night is greater than the thickness of the tissue/leaf the previous night, it may be an indicator of irrigation and/or an indicator of growth. If a reduction in the night thickness is detected and water/solute is applied to the tissue/plant, it is expected that the thickness recoups at its hydrated state. If this expectation is not observed, it can be a signal to an alternative issue to the tissue/plant, such as pests or excessive previous water/solute stress that inhibits the normal activity of the tissue/leaf to uptake water. As such, the systems described herein also can be used as a tool to monitor healthy behavior of the plant. If no water/solute is applied to the plant/tissue and still an increase is observed in the leaf thickness in comparison to the previous night, it is an indicator of the tissue growth which its magnitude can show the rate of the growth. The reverse behavior would be assumed as negative growth. Another approach is to compare the daily minimums to observe a dramatic/abnormal decrease in the minimums which is a signal of water stress. A study showed that relative leaf thickness is a function of soil water content, as the water input to the leaf, and evapotranspiration, as the water output from the leaf. This shows that monitoring the tissue/leaf thickness is a tool to observe the tissue/leaf water balance, or in other words, to monitor tissue/leaf/plant water status.

In embodiments where a capacitive tissue thickness sensor is used to obtain information from plant tissue, a measured change in the electrical capacitance of the capacitive plates may be used to determine plant tissue thickness. More specifically, the capacitive plates have a known capacitance when no material is inserted between the first and second pieces. However, insertion of material between the first and second pieces (e.g., insertion of plant tissue) may cause changes in the distance between the conductive component (dielectric material) and the capacitive plates, which causes a change in electrical capacitance between the capacitive plates. Such a change can be used as a gauge for leaf thickness, as described in greater detail herein.

In addition to measuring leaf thickness, it should further be understood that the description provided herein with respect to the tissue thickness sensor and/or the capacitive tissue thickness sensor may further be used to determine tissue growth and whether the tissue is bending by tracking the observed changes over a period of time. That is, the same tissue is measured as described herein at various intervals over a particular period of time to determine how the thickness of the tissue has changed, which can be used to determine growth of the tissue and/or whether the tissue is bending.

In some embodiments, the obtained measurements as described herein may be normalized. Normalization may be completed using raw data obtained from the sensing device and/or calibrated values. In some embodiments, normalizing measurement values may be completed for a maximum recorded value obtained from all values that have been obtained between a beginning of the data acquisition to a particular end measurement. For example, in embodiments where leaf thickness (LT) is measured (regardless of by magnets and a magnetic sensor or by capacitance measurements as described herein), the system described herein may be configured to always update a variable annotated as $LT_{max}$, which stores the maximum recorded leaf thickness. In other words, the system stores the first leaf thickness measurement into $LT_{max}$ and updates it whenever the leaf thickness measurement is larger ($LT>LT_{max}$). As a result, a relative leaf thickness may be a leaf thickness measurement that is normalized by $LT_{max}$. In some embodiments, normalizing the measurement value may be completed with the maximum recorded value within irrigation cycles, from the irrigation moment to the interested measurement. For example, in embodiments where leaf thickness is measured, the systems described herein may always update a variable annotated as $LT_{max,irr}$, which stores the maximum recorded leaf thickness within irrigation cycles. In other words, the systems described herein may store the first leaf thickness measurement into $LT_{max,irr}$ upon an irrigation. After the irrigation, the system updates $LT_{max,irr}$ whenever the leaf thickness measurement is larger than $LT_{min}$ ($LT>LT_{max,irr}$). As a result, a relative leaf thickness may be a leaf thickness measurement that is normalized by $LT_{max,irr}$. A similar concept may be applied to the tissue capacitance sensor. $CAP_{max}$ may be the maximum recorded capacitance by the tissue capacitance sensor and $CAP_{max,irr}$ may be the maximum recorded tissue capacitance within the irrigation cycles. The tissue capacitance measurements may be normalized by $CAP_{max}$ or $CAP_{max,irr}$.

It should be understood that the leaf thickness examples described above are merely illustrative, and a normalized leaf thickness may be achieved by raw data or calibrated data collected by the thickness measurement techniques based on the output of the magnetic field sensor or the capacitive method for thickness measurements. In other words, the above-described methods may be used for the raw data or calibrated measurements for leaf thickness (using a magnetic field sensor or a capacitive sensor). It should be understood that the capacitive sensors depicted in FIGS. 6A-6B and 7A-7B are for tissue thickness measurements, which is apart from the tissue capacitance sensor illustrated in FIG. 2. Therefore, normalized data based on the capacitive sensor for tissue thickness measurements provides normalized tissue thickness values (similar to the tissue thickness measurements based on the magnetic field sensor method), while the normalized data of the tissue capacitance sensor provides normalized tissue capacitance. It should further be understood that normalizing the data may assist in reducing variability due to factors other than plant water/solute status, such as growth and plant stress history.

In embodiments where a capacitive tissue sensor and a tissue thickness sensor are used to obtain information from plant tissue, the combined measurements may be used to determine a water/solute content. For example, night-time relative leaf thickness may be used to detect severe water stress levels, whereas noon-time relative leaf thickness may distinguish the early water stress levels but not middle and late stress levels. However, a noon-time relative capacitance may identify the mid-range water stress levels. As such, a combination of the relative values of the daily critical leaf thickness and capacitance measurements may provide an ability to detect each water/solute stress level.

Calculating may include, for example, predetermining quality, importance, and repeated signal weights. The quality weight may represent the quality of the measurement in relation to distinguishing the water stress levels. The information from relationships of relative leaf thickness and capacitance with soil water content ($\theta$) or water stress levels may be used for determining the quality weights. For example, the relationships between the night-time relative leaf thickness versus $\theta$ and water stress level ($RLT_{night}$-$\theta$ and $RLT_{night}$-stress level) may indicate stronger relationships compared to those of the noon-time relative leaf thickness ($RLT_{noon}$). Therefore, $RLT_{night}$ may have a greater quality weight than $RLT_{noon}$. This weight may be a function of relative leaf thickness or the relative capacitance. For example, the quality weight can be smaller for larger $RLT_{noon}$ values.

An importance weight may be based on the severity of the water stress level that relative leaf thickness or capacitance starts to be sensitive to water stress. For example, the means of $RLT_{night}$ may be substantially constant for the early water stress levels until the extreme stress level where $RLT_{night}$ decreased dramatically. Therefore, any change in $RLT_{night}$ may be interpreted as the occurrence of a severe water stress. Accordingly, the importance weight of $RLT_{night}$ may be larger than that of $RLT_{noon}$, which was sensitive to the early water stress levels.

The importance weight may also be a function of the relative measurement. For example, a range of $RLT_{night}$, from one (1) to a threshold, may be considered as a well-water stress level that brackets a range of $RLT_{night}$ errors when water stress is not detectable by $RLT_{night}$.

Therefore, the importance weight may be zero (0) for the range of $RLT_{night}$ from one (1) to the threshold. This weight may be greater than zero to represent the slope of the relative measurement variations for a given change in the water stress level.

The repeated signal weight may help to reduce the effect of outliers. In a practical application, it is expected that a leaf may expose an abnormal dynamics compared to others. For example, a leaf may be dried up as an outlier of the samples. The repeated signal weight will be small if water stress is detected by a single signal. The weight will rapidly increase by detection of water stress by one more signal. For example, the repeated signal weight can be an exponential function of the number of signals (or leaf sensors) that detected a specific water stress level. Therefore, the effect of an outlier will be minor by multiplying it to a small weight (repeated signal weight).

In a practical application, each relative leaf thickness and capacitance measurements for each leaf sensor may be multiplied by its proposed weights and the resulting products may be added for all the measurements and sensors as the water status index. Later, a threshold can be determined on this index as a critical water status for triggering the irrigation, as described in greater detail herein.

In some embodiments, the capacitive tissue sensor and/or the tissue thickness sensor (or the capacitive tissue thickness sensor) may not determine the dielectric constant of the tissue, determine tissue thickness, and/or determine the water content of the plant. Rather, the various components may merely obtain measurements and transmit (via the transceiver and/or the output terminal) raw data to the central unit. The central unit may then determine the dielectric constant of the tissue, determine tissue thickness, and/or determine the water content of the plant tissue based on the received measured capacitive signal. In addition, the central unit may also determine other plant tissue characteristics based upon the dielectric constant, such as, for example, various photosynthesis properties and/or stomatal conductance.

In various embodiments, the various measurements may further be used to determine a periodic plant water status. For example, the leaf thickness of a plant tissue may have daily variations. That is, leaf thickness may decrease during periods of light and may increase during periods of darkness. Accordingly, a minimum leaf thickness may occur close to noon (at the maximum ambient temperature and light intensity) and a maximum leaf thickness may occur at midnight. For capacitance, a minimum capacitance may occur during periods of darkness and a maximum capacitance may occur close to noon (at maximum light intensity). Such daily critical values may be extracted and used for estimation of plant water status ($LT_{noon}$, $LT_{night}$, $CAP_{night}$, and $CAP_{noon}$). In an automatic system, data collection intervals may be adjusted to collect data at the times of the day that the critical values are expected, such as, for example, at 1:00 pm and 2:00 am. This strategy may decrease a computational cost and a power consumption. These advantages may further reduce the electronic circuit costs (lower computational power) and also power consumption which is a critical feature for battery operated devices.

Once the water stress has been detected, the central unit may determine whether the amount of water supplied to the plant needs to be altered at step 1050. If so, the central unit may direct the irrigation control unit to adjust the amount of water supplied to the plant and/or the amount of light supplied to the plant at step 1060. In some embodiments, the central unit may direct the irrigation control unit to increase the amount of water supplied to the plant. In other embodiments, the central unit may direct the irrigation control unit to decrease the amount of water supplied to the plant. If the amount of water does not need to be altered, the process may return to step 1020 for further monitoring. Likewise, once the amount of water and/or light supplied to the plant tissue has been altered, the process may also return to step 1020 for further monitoring, thereby allowing continuous monitoring of the plant tissue.

Figure 11:
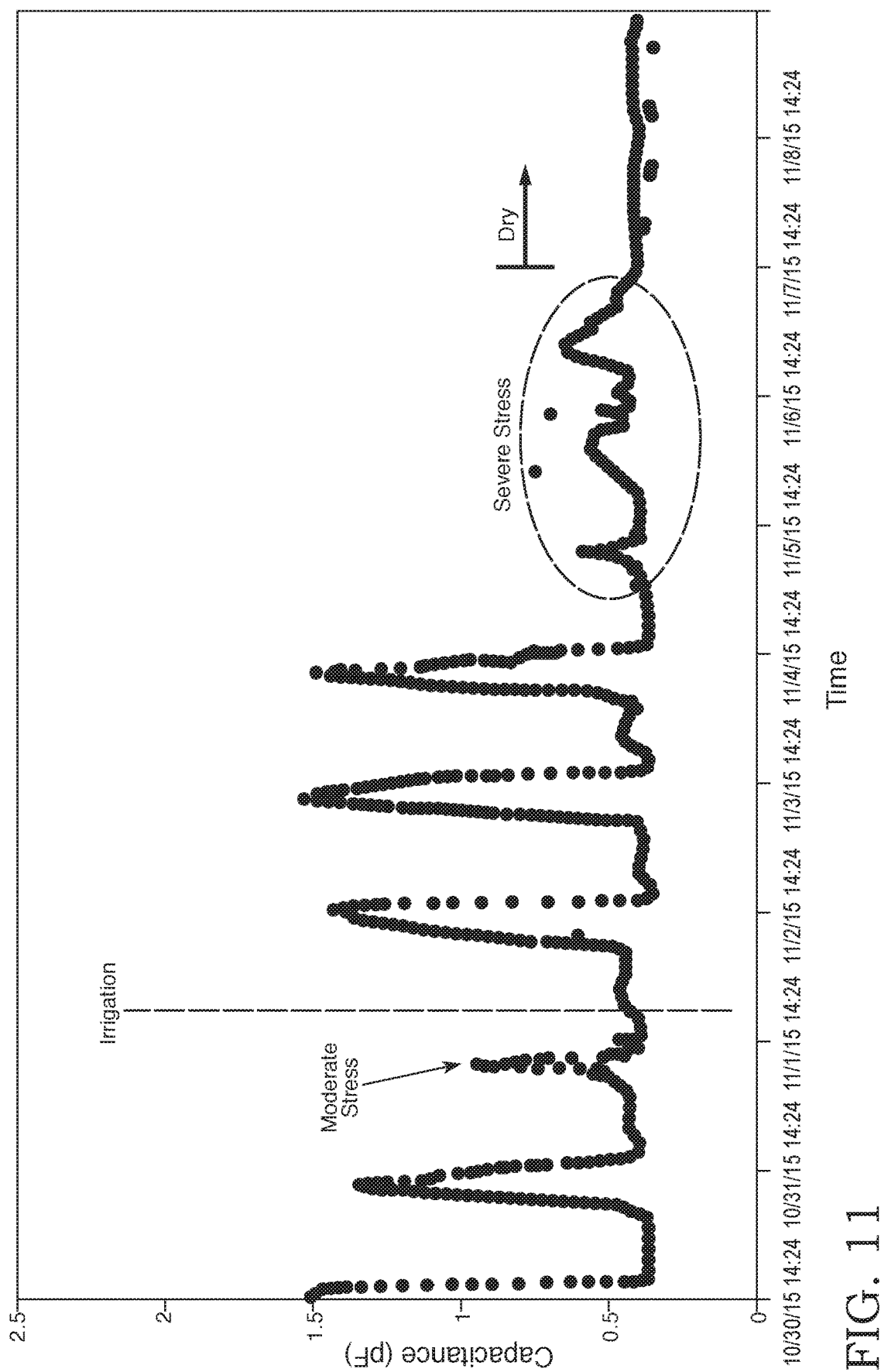
FIG. 11 graphically depicts output dynamics of a sensing device including a capacitive tissue sensor according to one or more embodiments shown and described herein.

In some embodiments, instead of using actual sensor readings, an analysis of the output dynamics may help to obtain information about the state of the plant. In this approach, the characteristics of the trend (slope, picks, curvature, and turning points) are analyzed to mine information and detect the critical moments. This method helps to eliminate the crop specific calibrations. An illustrative image of output dynamics of the capacitive tissue sensor on a plant are shown in FIG. 11.

The steps described herein may be completed on live plant tissue that is still connected to a live plant. In some embodiments, the steps described herein may be completed in an outdoor field environment. In other embodiments, the steps described herein may be completed in an indoor environment, such as, for example, a greenhouse environment and/or a laboratory environment.

In some embodiments, the steps described herein may be used for measuring solute/sugar content of particular plant tissue, such as, sap and/or fruits. For fruits, such a measurement may be used for determining the ripeness of the fruit.

Accordingly, it should now be understood that the systems, devices, and methods described herein allow for a non-invasive determination of water content of plant tissue. The systems described herein include a capacitive tissue sensor that clips onto the plant tissue, and a capacitor portion of the capacitive tissue sensor generates and transmits a capacitive signal via coplanar conductive plates through the plant tissue to measure a dielectric constant of the plant tissue. The dielectric constant can be used to determine the water content/status and photosynthetic activity of the plant tissue. Once the water content has been determined, a determination may be made as to whether the plant requires an adjustment in the irrigation time and the amount of water supplied to the plant. The water supply to the plant may then be adjusted accordingly. The systems, devices, and methods described herein are non-invasive such that they do not damage the plant tissue to which the capacitive tissue sensor is attached. This is completed by using clear and/or flexible material in the various components of the capacitive tissue sensor such that electromagnetic radiation can passed through the capacitive tissue sensor to the plant and plant transpiration is still allowed with the capacitive tissue sensor attached.

It should now also be understood that the systems, devices, and methods described herein allow for a non-invasive determination of water content of plant tissue. The apparatus described herein includes a clip with two magnetic devices that produce a magnetic field therebetween. Alteration of the magnetic field by placement of plant tissue between the magnets is sensed by a sensor, which is then used to determine a dimensional aspect (e.g., thickness) of the plant tissue. The thickness of the plant tissue can be correlated to the amount of water (i.e., water content) present in the cells of the plant tissue. Once the water content has been determined, a determination may be made as to whether the plant requires an adjustment in the irrigation time and the amount of water supplied to the plant. The water supply to the plant may then be adjusted accordingly.

The systems, devices, and methods described herein are non-invasive such that they do not damage the plant tissue to which the measuring apparatus is attached.

Additional Related Information

Photosynthesis

The chemical equation of photosynthesis is:

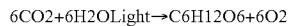

In this process, light provides the energy to produce glucose (C6H12O6). Therefore, it is expected to observe a sinusoid pattern in the capacitance dynamics of the sensor in response to the day and night light intensity changes. The evaluation of the sensor on tomato plants in a greenhouse showed the similar pattern. The capacitance increased by sunrise till about noon and after that showed a decaying pattern. The capacitance was constant during nights. The pick of the curve was decreased by increasing the level of water stress. Extreme water stress resulted in to smooth the dynamics to a line. In other words, the capacitance was constant at the minimum without any dynamics when it was extremely stressed.

The current methods of measuring photosynthetic activity are working based on the mentioned chemical equation. These methods either measure the reduction in atmospheric $CO_2$ concentration, an increase in $O_2$ concentration, or the produced mass.

$CO_2$ uptake can be measured by IRGA devices such as LI-6400XT, which can compare the $CO_2$ concentration in the gas passing into a chamber surrounding a leaf/plant and the $CO_2$ leaving the chamber. The difference shows how much $CO_2$ is used in the photosynthesis. In other words, the more difference between the input and output $CO_2$, the more photosynthetic activity.

Oxygen can be measured by counting bubbles evolved from pondweed, or by using Audus apparatus to measure the amount of gas evolved over a period of time. The more produced $O_2$, the more photosynthetic activity.

There is a crude method where a disc is cut out of one side of a leaf (using a cork borer against a rubber bung) and weighed after drying. Some days (or even weeks) later, a disk is cut out of the other half of the leaf, dried and weighed. An increase in the mass of the disc is an indication of the extra mass that has been stored in the leaf.

Dry mass is often monitored by the technique of 'serial harvests' where several plants are harvested, dried and weighed. This is repeated over the duration of the experiment.

In addition to its use as a tracer in photosynthetic pathways, the radioactive isotope $^{14}C$ has also been, and continues to be, used in many studies for measuring photosynthetic rate. The most common method involves enclosing a leaf or algal suspension in a sealed transparent chamber and exposing it to a mixture of $^{12}CO_2$ and $^{14}CO_2$ in which both the total $CO_2$ and the specific activity of $^{14}CO_2$ are known. The chamber is illuminated to activate $CO_2$ fixation, and the time of exposure to $^{14}CO_2$ is measured.

Stomatal Conductance

Stomata is the gate of leaf to the atmosphere for passing gasses and vapor. The conductance of gas and vapor passage through stomata is called stomatal conductance. The plant responds to water stress by stomatal closure stimulated by osmotic adjustment to reduce transpiration. Therefore, stomatal closure reduces the amount of water vapor transpired to the atmosphere. Principally, the methods of measuring stomatal conductance are based on changes in relative humidity (RH) or the leaf temperature.

Porometer provides a rapid measurement of leaf stomatal conductance in irrigated trials, though it is not a recommended measurement under water stress (unless very mild) as the stomata are generally closed. An effectively open chamber is secured to the leaf surface and water vapor released through the stomata sets up an RH gradient along the chamber. The instrument monitors RH at two points along the flux path and, once the flux gradient reaches a steady state, it calculates and displays the leaf diffusion conductance (the reciprocal of resistance). A leaf with a rapidly changing gradient indicates that the stomata are relatively open. LI-6400XT (IRGA) also measures stomatal conductance by the same approach.

The other technique is to measure leaf temperature. Transpiration reduces the leaf temperature by latent heat transfer. Therefore, the less stomatal conductance results in less transpiration and a higher leaf temperature accordingly. The current methods of estimating stomatal conductance by this method are measuring leaf temperature by remote or contact approaches (e.g. using NIR measurements or by attaching temperature sensors on a leaf).

The invention claimed is:

1. A system for non-invasively determining a dimensional aspect of plant tissue, the system comprising:
  a sensing device comprising a first piece and a second piece, wherein the first piece and the second piece are coupled together to form a clip;
  a tissue thickness sensor disposed between the first piece and the second piece, wherein the tissue thickness sensor comprises:
    a first permanent magnet,
    a second permanent magnet, and
    a magnetic sensor,
    wherein:
      a first magnetic field generated between the first permanent magnet and the second permanent magnet creates a repulsive magnetic force between the first piece and the second piece,
      a second magnetic field generated by the second permanent magnet reduces an offset magnetic field generated by the first permanent magnet; and
      the magnetic sensor is positioned in a location such that a strength of the magnetic field can be sensed, wherein when the plant tissue is placed between the first piece and the second piece, a change in the strength of the magnetic field is sensed by the magnetic sensor and the dimensional aspect is determined based on the change in the strength.

2. The system of claim 1, wherein the first piece and the second piece are coupled together via a hinge that biases the first piece and the second piece towards each other.

3. The system of claim 1, wherein the first permanent magnet is disposed on the first piece and the second permanent magnet is disposed on the second piece.

4. The system of claim 1, wherein at least one of the first piece and the second piece is constructed of a clear, flexible material.

5. The system of claim 1, wherein at least one of the first piece and the second piece are formed of a material that allows at least some electromagnetic radiation to pass therethrough.

6. The system of claim 1, wherein at least one of the first piece and the second piece are formed of a material that allows for transpiration of the plant tissue when the system is placed on the plant tissue.

7. The system of claim 1, wherein the first permanent magnet is a variable distance magnet and the second permanent magnet is a bias permanent magnet.

8. The system of claim 1, wherein the magnetic sensor is a magnetoresistive sensor.

9. The system of claim 1, wherein the magnetic sensor is a Hall-effect sensor.

10. The system of claim 1, wherein the dimensional aspect is a thickness of the plant tissue.

11. A system for non-invasively determining one or more of a water content, a solute content, and a thickness of plant tissue, the system comprising:
a sensing device comprising a first piece and a second piece, wherein the first piece and the second piece are coupled together to form a clip; a capacitive tissue sensor comprising a capacitor having a plurality of coplanar conductive plates,
wherein the first piece and the second piece are biased in a closed position to provide a gripping force around the plant tissue such that at least a portion of the plant tissue contacts the plurality of coplanar conductive plates; and
a tissue thickness sensor disposed between the first piece and the second piece, wherein the tissue thickness sensor comprises:
a first permanent magnet,
a second permanent magnet, and
a magnetic sensor,
wherein:
a first magnetic field generated between the first permanent magnet and the second permanent magnet create a repulsive magnetic force between the first piece and the second piece,
a second magnetic field generated by the second permanent magnet reduces an offset magnetic field generated by the first permanent magnet; and
the magnetic sensor is positioned in a location such that a strength of the magnetic field can be sensed, wherein when the plant tissue is placed between the first piece and the second piece, a change in the strength of the magnetic field is sensed by the magnetic sensor and the dimensional aspect is determined based on the change in the strength.

12. The system of claim 11, wherein at least one of the first piece and the second piece is constructed of a clear, flexible material.

13. The system of claim 11, wherein at least one of the first piece and the second piece are formed of a material that allows at least some electromagnetic radiation to pass therethrough.

14. The system of claim 11, wherein at least one of the first piece and the second piece are formed of a material that allows for transpiration of the plant tissue when the system is placed on the plant tissue.

15. The system of claim 11, wherein the capacitive tissue sensor further comprises a printed circuit board disposed on a surface of the second piece.

16. The system of claim 11, wherein the capacitive tissue sensor further comprises a printed circuit board integrated with the second piece.

17. The system of claim 11, wherein the capacitive tissue sensor further comprises measuring circuitry coupled to the plurality of coplanar conductive plates.

18. The system of claim 11, wherein the capacitive tissue sensor further comprises an output terminal coupled to the plurality of coplanar conductive plates and communicatively coupled to a central unit comprising a processing device.

19. The system of claim 11, further comprising a protective material disposed on the capacitive tissue sensor.

* * * * *